(12) United States Patent
Verhoef et al.

(10) Patent No.: US 12,580,057 B2
(45) Date of Patent: *Mar. 17, 2026

(54) SYSTEMS AND METHODS FOR NATURAL LANGUAGE PROCESSING-BASED CLASSIFICATION OF ELECTRONIC MEDICAL RECORDS

(71) Applicant: egnite, Inc., Aliso Viejo, CA (US)

(72) Inventors: Kahla Verhoef, San Clemente, CA (US); Michelle Kwon, Wayne, PA (US)

(73) Assignee: egnite, Inc., Aliso Viejo, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 18/781,208

(22) Filed: Jul. 23, 2024

(65) Prior Publication Data

US 2025/0149132 A1 May 8, 2025

Related U.S. Application Data

(63) Continuation of application No. 18/386,750, filed on Nov. 3, 2023.

(51) Int. Cl.
| | |
|---|---|
| *G16H 10/60* | (2018.01) |
| *G06F 40/205* | (2020.01) |
| *G06F 40/284* | (2020.01) |

(52) U.S. Cl.
CPC ........... *G16H 10/60* (2018.01); *G06F 40/205* (2020.01); *G06F 40/284* (2020.01)

(58) Field of Classification Search
CPC ...... G16H 10/60; G06F 40/284; G06F 40/205
See application file for complete search history.

(56) References Cited

U.S. PATENT DOCUMENTS 7,937,263 B2 * 5/2011 Carrier .................. G06F 40/284
704/10
11,361,162 B2 * 6/2022 Cook .................... G06F 40/284
(Continued)

FOREIGN PATENT DOCUMENTS

JP         2024085141 A  *  6/2024  ........... G06T 7/0016
WO    WO-2018200274 A1 * 11/2018  ............. G06F 40/30
(Continued)

*Primary Examiner* — Mamon Obeid
*Assistant Examiner* — Pierre L Maccagno
(74) *Attorney, Agent, or Firm* — Greenberg Traurig LLP; Chinh H. Pham; Kristopher Reichlen

(57) ABSTRACT

Systems and methods of the present disclosure enable improved natural language processing of patient-related medical information for clinical decision support. To do so, a processor receives patient data including a written report, and accesses a dictionary of terminology associated with a disease. The terminology includes descriptors indicative of categories of the disease. The processor inputs the written report into a tokenization function to output tokens by parsing word patterns in the written report, and generating the tokens from the word patterns. The processor determines a presence in the written report of each descriptor based on the tokens and determines a category-specific score associated with each category based on the presence of the descriptors. The processor determines a category recommendation score indicative of a particular category based on the category-specific scores and generates a category recommendation representing the particular category based on the category recommendation score.

18 Claims, 10 Drawing Sheets

(56)             References Cited

U.S. PATENT DOCUMENTS

| 11,521,723 | B2 * | 12/2022 | Liu | G16H 40/40 |
|---|---|---|---|---|
| 2006/0116862 | A1 * | 6/2006 | Carrier | G06F 40/284 |
| | | | | 704/1 |
| 2014/0278478 | A1 * | 9/2014 | Vezina | A61B 5/0006 |
| | | | | 705/2 |
| 2014/0372148 | A1 | 12/2014 | Reddy | |
| 2016/0188601 | A1 * | 6/2016 | Ganesamoorthi | G06Q 50/01 |
| | | | | 705/2 |
| 2019/0057068 | A1 * | 2/2019 | Diamond | G06F 40/197 |
| 2022/0164535 | A1 * | 5/2022 | Berns | G06F 40/284 |
| 2023/0123711 | A1 * | 4/2023 | De Peuter | G06F 40/284 |
| | | | | 704/9 |
| 2023/0309967 | A1 * | 10/2023 | Vaid | A61B 8/5223 |
| | | | | 600/408 |

FOREIGN PATENT DOCUMENTS

| WO | WO-2020006495 | A1 * | 1/2020 | G16H 50/20 |
|---|---|---|---|---|
| WO | WO-2020126868 | A1 * | 6/2020 | G06F 40/40 |
| WO | WO-2024077058 | A1 * | 4/2024 | G06F 16/3344 |

* cited by examiner

| Secondary MR Descriptors | Primary Degenerative MR Descriptors | | | |
|---|---|---|---|---|
| | Tier 1<br>Primary, degenerative, prolapse, flail, myxomatous, Barlow's, ruptured chord(ae), fibroelastic (deficiency) | Tier 2<br>Leaflet calcification (moderate or greater) | Tier 3<br>Leaflet thickening, valve thickening, leaflet calcification (less than moderate/unspecified), mitral cleft, annular calcification | Unknown (no eligible descriptors found) |
| Tier 1<br>Secondary, ischemic (but not ischemic cardiomyopathy), functional | Mixed | Mixed | Secondary | Secondary |
| Tier 2<br>Leaflet tethering or restriction; severe LV dilation, enlargement, or cavity enlargement; severe systolic LV dysfunction or reduced function; dilated cardiomyopathy; ischemic cardiomyopathy | Primary degenerative if EF ≥ 50%<br>Mixed if EF < 50% | Primary degenerative if EF ≥ 50%<br>Mixed if EF < 50% | Mixed if EF ≥ 50%<br>Secondary if EF < 50% | Secondary |
| Tier 3<br>LV dilation, enlargement, or cavity enlargement (less than severe/unspecified); systolic LV dysfunction or reduced function (less than severe/unspecified); central MR; annular dilation; LA enlargement or dilation | Primary degenerative | Primary degenerative if EF ≥ 50%<br>Mixed if EF < 50% | Unknown | Unknown if EF ≥ 50%<br>Secondary if EF < 50% |
| Unknown (no eligible descriptors found) | Primary degenerative | Primary degenerative if EF ≥ 50%<br>Unknown if EF < 50% | Primary degenerative if EF ≥ 50%<br>Unknown if EF < 50% | Unknown |

FIG. 4

Primary Degenerative MR Descriptors

| Secondary MR Descriptors | Tier 1: Primary, degenerative, prolapse, flail, myxomatous, Barlow's, ruptured chord(ae), fibroelastic (deficiency) | Tier 2: Leaflet calcification (moderate or greater) | Tier 3: Leaflet thickening, valve thickening, leaflet calcification (less than moderate/unspecified), mitral cleft, annular calcification | Unknown (no eligible descriptors found) |
|---|---|---|---|---|
| Tier 1 Secondary, ischemic (but not ischemic cardiomyopathy), functional | Mixed | Mixed | Secondary | Secondary |
| Tier 2 Leaflet tethering or restriction; severe LV dilation, enlargement, or cavity enlargement; severe systolic LV dysfunction or reduced function; dilated cardiomyopathy; ischemic cardiomyopathy | Primary degenerative if EF ≥ 50% Mixed if EF < 50% | Unknown | Unknown | Secondary if EF < 50% Unknown if EF ≥ 50% |
| Tier 3 LV dilation, enlargement, or cavity enlargement (less than severe/unspecified); systolic LV dysfunction or reduced function (less than severe/unspecified); central MR; annular dilation; LA enlargement or dilation | Primary degenerative | Unknown | Unknown | Unknown |
| Unknown (no eligible descriptors found) | Primary degenerative | Primary degenerative if EF ≥ 50% Unknown if EF < 50% | Unknown | Unknown |

FIG. 5

SYSTEMS AND METHODS FOR NATURAL LANGUAGE PROCESSING-BASED CLASSIFICATION OF ELECTRONIC MEDICAL RECORDS

RELATED APPLICATION(S)

This application is a continuation patent application of U.S. application Ser. No. 18/386,750, filed Nov. 3, 2023, the contents of which is incorporated herein by reference in its entirety.

FIELD OF TECHNOLOGY

The present disclosure generally relates to computer-based systems, computing devices and/or computing objects configured for improved natural language processing (NLP) of electronic records including electronic medical records to enable automatic clinical recommendations.

BACKGROUND OF TECHNOLOGY

Many diseases may include classifications of types, mechanisms, severity, among other delineations of subsets of a given disease. Indeed, the ACC/AHA Guidelines and Clinical Documents for various diseases stress the importance of determining the subset so as to enable informed and effective treatment. Guidance on how to classify some diseases may be complex and delineation of the mechanism of disease is often inconsistently documented or not explicit in medical reports.

SUMMARY

In some aspects, the techniques described herein relate to a method, including: receiving, by at least one processor, patient data including at least one written report associated with at least one patient; accessing, by the at least one processor, a dictionary of terminology associated with at least one disease; wherein the terminology includes a plurality of descriptors; wherein each descriptor is indicative of at least one category of a plurality of categories associated with the at least one disease; wherein each descriptor is associated with at least one descriptor-specific score representative of a relevance to the at least one category; inputting, by the at least one processor, the at least one written report into a tokenization function to output a set of tokens, wherein the tokenization function is configured to: parse at least one word pattern in the at least one written report, and generate the set of tokens from the at least one word pattern; determining, by the at least one processor, a presence in the at least one written report of each descriptor of the plurality of descriptors based at least in part on the set of tokens associated with the at least one written report; determining, by the at least one processor, a category-specific score of a plurality of category-specific scores associated with each category of the plurality of categories based at least in part on: the presence of each descriptor of the plurality of descriptors and the at least one descriptor-specific score of each descriptor; determining, by the at least one processor, at least one category recommendation score indicative of at least one particular category based at least in part on the category-specific score associated with each category; generating, by the at least one processor, at least one category recommendation representing the at least one particular category for the at least one patient based at least in part on the at least one category recommendation score; and rendering, by the at least one processor, an output to a display associated with the at least one patient to present to a user at least one category recommendation associated with the at least one category recommendation score so as to provide clinical decision support.

In some aspects, the techniques described herein relate to a method, further including: inputting, by the at least one processor, each descriptor of the plurality of descriptors into the tokenization function to output a set of descriptor tokens; and searching, by the at least one processor, the set of tokens with the set of descriptor tokens to identify occurrences of each descriptor based at least in part on a match of at least one descriptor token of each descriptor to at least one token of the written report.

In some aspects, the techniques described herein relate to a method, wherein the plurality of descriptors include a plurality of combinations of a plurality of descriptor tokens, wherein each combination of the plurality of combinations represents a particular descriptor of the plurality of descriptors.

In some aspects, the techniques described herein relate to a method, wherein the plurality of combinations and the plurality of descriptor tokens are hand-crafted.

In some aspects, the techniques described herein relate to a method, wherein the at least one disease includes mitral regurgitation.

In some aspects, the techniques described herein relate to a method, wherein the plurality of categories associated with mitral regurgitation includes: a primary degenerative mitral regurgitation category indicative of primary degenerative mitral regurgitation, and a secondary mitral regurgitation category indicative of secondary mitral regurgitation; and wherein the plurality of category-specific scores associated with mitral regurgitation includes: a primary degenerative mitral regurgitation score associated with the primary degenerative mitral regurgitation category, and a secondary mitral regurgitation score associated with the secondary mitral regurgitation category.

In some aspects, the techniques described herein relate to a method, further including: determining the at least one category recommendation as mixed mitral regurgitation indicative of a combination of the primary degenerative mitral regurgitation and the secondary mitral regurgitation based at least in part on the primary degenerative mitral regurgitation score indicating a presence of primary degenerative mitral regurgitation and the secondary mitral regurgitation score indicating a presence of secondary mitral regurgitation.

In some aspects, the techniques described herein relate to a method, further including: determining the at least one category recommendation as unknown mitral regurgitation based at least in part on the primary degenerative mitral regurgitation score not indicating a presence of primary degenerative mitral regurgitation and the secondary mitral regurgitation score not indicating a presence of secondary mitral regurgitation.

In some aspects, the techniques described herein relate to a method, further including: determining, by the at least one processor, at least one category recommendation score indicative of the at least one particular category based at least in part on: the category-specific score associated with each category, and at least one medical test result.

In some aspects, the techniques described herein relate to a method, further including: determining, by the at least one processor, at least one category recommendation score indicative of the at least one particular category based at least in part on: the category-specific score associated with each category, and a set of classification parameters for balancing each category-specific score so as to select a particular category of the plurality of categories.

In some aspects, the techniques described herein relate to a system including: at least one processor in communication with at least one non-transitory computer readable medium having software instructions stored thereon, wherein, upon execution of the software instructions, the at least one processor is configured to: receiving, by at least one processor, patient data including at least one written report associated with at least one patient; access a dictionary of terminology associated with at least one disease; wherein the terminology includes a plurality of descriptors; wherein each descriptor is indicative of at least one category of a plurality of categories associated with the at least one disease; wherein each descriptor is associated with at least one descriptor-specific score representative of a relevance to the at least one category; input the at least one written report into a tokenization function to output a set of tokens, wherein the tokenization function is configured to: parse at least one word pattern in the at least one written report, and generate the set of tokens from the at least one word pattern; determine a presence in the at least one written report of each descriptor of the plurality of descriptors based at least in part on the set of tokens associated with the at least one written report; determine a category-specific score of a plurality of category-specific scores associated with each category of the plurality of categories based at least in part on: the presence of each descriptor of the plurality of descriptors and the at least one descriptor-specific score of each descriptor; determine at least one category recommendation score indicative of at least one particular category based at least in part on the category-specific score associated with each category; generate at least one category recommendation representing the at least one particular category for the at least one patient based at least in part on the at least one category recommendation score; and render an output to a display associated with the at least one patient to present to a user at least one category recommendation associated with the at least one category recommendation score so as to provide clinical decision support.

In some aspects, the techniques described herein relate to a system, wherein, upon execution of the software instructions, the at least one processor is further configured to: input each descriptor of the plurality of descriptors into the tokenization function to output a set of descriptor tokens; and search the set of tokens with the set of descriptor tokens to identify occurrences of each descriptor based at least in part on a match of at least one descriptor token of each descriptor to at least one token of the written report.

In some aspects, the techniques described herein relate to a system, wherein the plurality of descriptors include a plurality of combinations of a plurality of descriptor tokens, wherein each combination of the plurality of combinations represents a particular descriptor of the plurality of descriptors.

In some aspects, the techniques described herein relate to a system, wherein the plurality of combinations and the plurality of descriptor tokens are hand-crafted.

In some aspects, the techniques described herein relate to a system, wherein the at least one disease includes mitral regurgitation.

In some aspects, the techniques described herein relate to a system, wherein the plurality of categories associated with mitral regurgitation includes: a primary degenerative mitral regurgitation category indicative of primary degenerative mitral regurgitation, and a secondary mitral regurgitation category indicative of secondary mitral regurgitation; and wherein the plurality of category-specific scores associated with mitral regurgitation includes: a primary degenerative mitral regurgitation score associated with the primary degenerative mitral regurgitation category, and a secondary mitral regurgitation score associated with the secondary mitral regurgitation category.

In some aspects, the techniques described herein relate to a system, wherein, upon execution of the software instructions, the at least one processor is further configured to: determine the at least one category recommendation as mixed mitral regurgitation indicative of a combination of the primary degenerative mitral regurgitation and the secondary mitral regurgitation based at least in part on at least one of: the primary degenerative mitral regurgitation score indicating a presence of primary degenerative mitral regurgitation and the secondary mitral regurgitation score indicating a presence of secondary mitral regurgitation, or In some aspects, the techniques described herein relate to a system, wherein, upon execution of the software instructions, the at least one processor is further configured to: determine the at least one category recommendation as unknown mitral regurgitation based at least in part on the primary degenerative mitral regurgitation score not indicating a presence of primary degenerative mitral regurgitation and the secondary mitral regurgitation score not indicating a presence of secondary mitral regurgitation.

In some aspects, the techniques described herein relate to a system, wherein, upon execution of the software instructions, the at least one processor is further configured to: determine at least one category recommendation score indicative of the at least one particular category based at least in part on: the category-specific score associated with each category, and at least one medical test result.

In some aspects, the techniques described herein relate to a system, wherein, upon execution of the software instructions, the at least one processor is further configured to: determine at least one category recommendation score indicative of the at least one particular category based at least in part on: the category-specific score associated with each category, and a set of classification parameters for balancing each category-specific score so as to select a particular category of the plurality of categories.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

FIG. 4 depicts an illustrative maximal (population capture) clinician-defined tiered rules-based framework for NLP of diagnosed MR mechanism in echocardiographic reports at scale in accordance with one or more embodiments of the present disclosure.

FIG. 5 depicts an illustrative minimal (highest-confidence capture only) clinician-defined tiered rules-based framework for NLP of diagnosed MR mechanism in echocardiographic reports at scale in accordance with one or more embodiments of the present disclosure.

DETAILED DESCRIPTION

Figure 1:
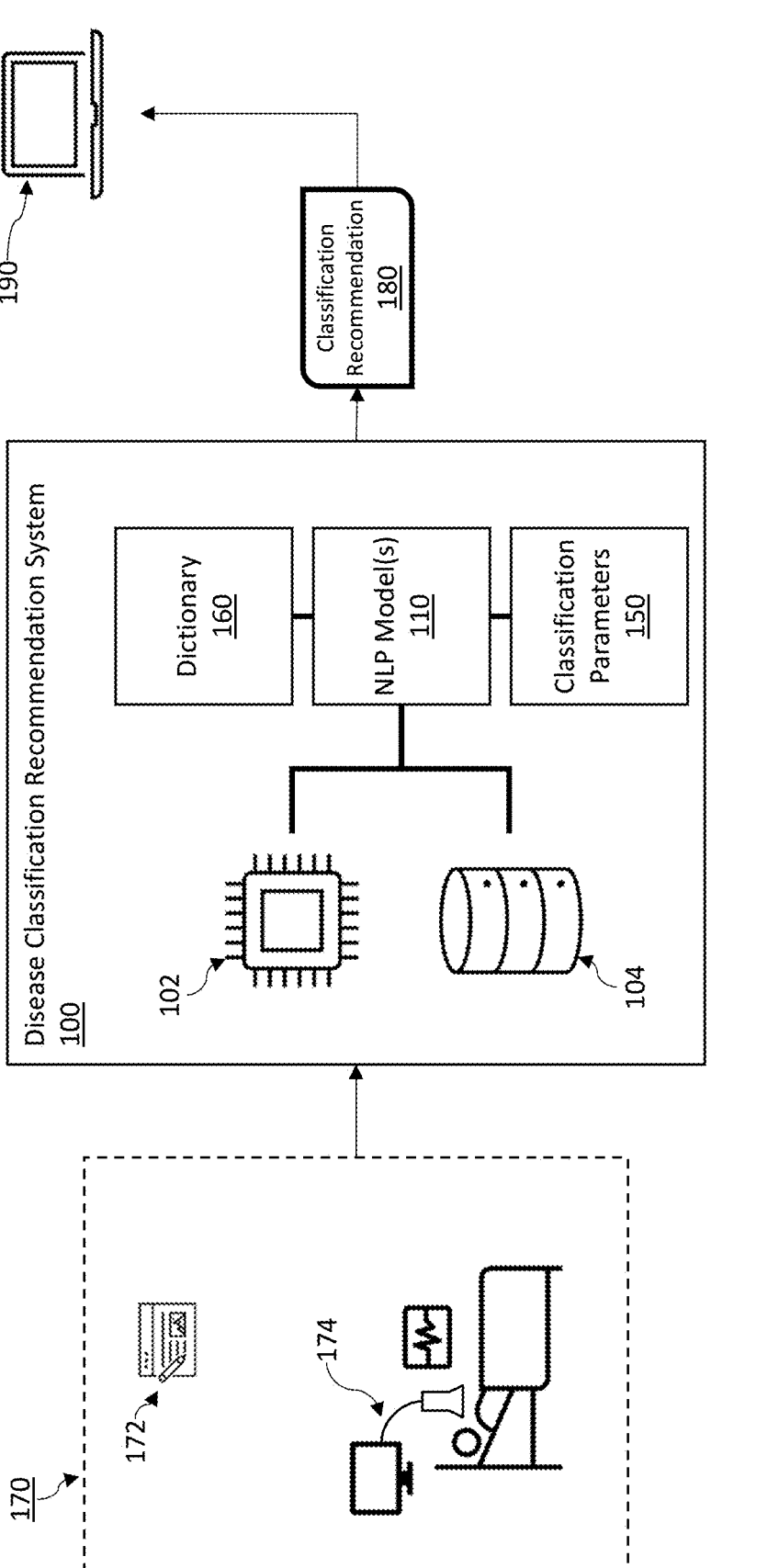
FIG. 1 depicts a disease classification recommendation system employing NLP to recommend a patient classification regarding one or more diagnoses in medical reports at scale in accordance with one or more embodiments of the present disclosure.

Various detailed embodiments of the present disclosure, taken in conjunction with the accompanying FIGs., are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the terms "and" and "or" may be used interchangeably to refer to a set of items in both the conjunctive and disjunctive in order to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

FIGS. 1 through 10 illustrate systems and methods of NLP applied to patient medical records. The following embodiments provide technical solutions and technical improvements that overcome technical problems, drawbacks and/or deficiencies in the technical fields involving clinical support recommendations and guidance using automated processes such as NLP, including technical fields involving identification and categorization based on documented disease diagnosis and/or mechanism of disease and guidance using automated processes such as NLP. Typical techniques for NLP often use resource heavy neural network algorithms or keyword searching that is incapable of reliably capturing nuance and variation in descriptions of some concepts such as a mechanism of a disease and/or condition. As explained in more detail, below, technical solutions and technical improvements herein include aspects of improved hierarchical rule-based language processing using a curated and/or learned dictionary of hierarchical indicator words that enable recommendations and/or predictions with improved resource consumption relative to machine learning models and improved accuracy relative to typical keyword searches. Based on such technical features, further technical benefits become available to users and operators of these systems and methods. Moreover, various practical applications of the disclosed technology are also described, which provide further practical benefits to users and operators that are also new and useful improvements in the art.

Referring to FIG. 1, a disease classification recommendation system employing NLP to recommend a patient classification regarding one or more diagnoses in medical reports at scale in accordance with one or more embodiments of the present disclosure.

In some embodiments, a user may access a disease classification recommendation system 100 via a user computing device 190. In some embodiments, the disease classification recommendation system 100 may provide to the user computing device 190 one or more disease classification recommendations 180 based on patient data 170 of a patient.

In some embodiments, the patient data 170 may include written reports 172, medical measurements 174 such as imagery and/or physiological measurements, among other data or any combination thereof. In some embodiments, the imagery may include one or more of echocardiographic reports, computer-aided tomography (CT) scans, x-ray imagery, magnetic resonance imaging (MRI) imagery, among other radiological or other imagery of a patient. In some embodiments, the physiological measurements may include documented size and thickness of the heart's chambers and walls, heart rate, respiration rate, heart rate variability, blood pressure, blood oxygen level, blood sugar level, diagnostic testing, genetic profiles, among others or any combination thereof. In some embodiments, imagery such as echocardiographic reports may include data and/or documented measurements such as the size and thickness of the heart's chambers and/or walls, as well as associated written reports and assessments by a doctor, technician, nurse, or other healthcare professional. In some embodiments, the disease classification recommendation system 100 may use NLP to process data associated with the imagery, such as the documented measurements related to the heart and associated written reports, but not the imagery itself. Accordingly, the disease classification recommendation system 100 analyzes written or other language-based information within the patient data 170, while healthcare professionals may access the patient data 170 to view both the language-based information as well as the imagery.

In some embodiments, the written reports 172 may include user provided information into digital and/or physical forms, documents, or other structures or any combination thereof. In some embodiments, the written reports 172 may include unstructured text, electronically input or scanned from a physical form. For example, the written reports 172 may include a doctor's description of finding in a radiological scan, from a patient visit, or other source or any combination thereof. In some embodiments, the written reports 172 may include structured information, such as predefined options, key-value pairs, information encoded into a vector, array, matrix, list or other structure, or any other structured data or any combination thereof, embodied in digital and/or physical form. For example, the structured information may include patient name, age, birth date, sex, physiological measurements, texts, test results, among other information encoded in one or more data structures or any combination thereof.

In some embodiments, the patient data 170 may be input to the disease classification recommendation system 100 by a user, including a doctor, nurse, patient, or other user or any combination thereof. In some embodiments, the patient data 170 may be accessed in an electronic health records (EHR) database and/or service, e.g., via application programming interface (API) or other computer interface technology.

In some embodiments, one or more interfaces may utilize one or more software computing interface technologies, such as, e.g., RESTful APIs, gRPC, WebSockets, GraphQL, an application programming interface (API) and/or application binary interface (ABI), among others or any combination thereof. In some embodiments, an API and/or ABI defines the kinds of calls or requests that can be made, how to make the calls, the data formats that should be used, the conventions to follow, among other requirements and constraints. An "application programming interface" or "API" can be entirely custom, specific to a component, or designed based on an industry-standard to ensure interoperability to enable modular programming through information hiding, allowing users to use the interface independently of the implementation.

In some embodiments, one or more interfaces may utilize one or more hardware computing interface technologies, such as, e.g., Universal Serial Bus (USB), IEEE 1394 (FireWire), Ethernet, Thunderbolt™, Serial ATA (SATA) (including eSATA, SATAe, SATAp, etc.), among others or any suitable combination thereof.

In some embodiments, the disease classification recommendation system 100 may obtain via the one or more interfaces and/or via user input, the patient data 170 and produce the disease classification recommendation 180. In some embodiments, the disease classification recommendation 180 may include a recommendation for assistance in diagnosis, patient identification, trial enrollment qualification, among other applications or any combination thereof. In some embodiments, the disease classification recommendation 180 may be provided to a clinician to aid in the clinicians review of the patient data 170. Such review may include secondary clinician review to verify the disease classification recommendation 180. For example, the disease classification recommendation 180 may include a recommendation or suggestion for identifying a particular patient a disease or disease mechanism, severity, stage or other categorization or any combination thereof.

In some embodiments, to generate the recommendation, the disease classification recommendation system 100 may use one or more NLP model(s) 110 to parse the patient data 170 and generate the recommendation. To do so, the disease classification recommendation system 100 may include hardware and/or software component to apply the NLP model(s) 110 to the patient data 170. In some embodiments, the disease classification recommendation system 100 may include hardware components such as a processor 102, which may include local or remote processing components. In some embodiments, the processor 102 may include any type of data processing capacity, such as a hardware logic circuit, for example an application specific integrated circuit (ASIC) and a programmable logic, or such as a computing device, for example, a microcomputer or microcontroller that include a programmable microprocessor. In some embodiments, the processor 102 may include data-processing capacity provided by the microprocessor. In some embodiments, the microprocessor may include memory, processing, interface resources, controllers, and counters. In some embodiments, the microprocessor may also include one or more programs stored in memory.

Similarly, the disease classification recommendation system 100 may include data store 104, such as one or more local and/or remote data storage solutions such as, e.g., local hard-drive, solid-state drive, flash drive, database or other local data storage solutions or any combination thereof, and/or remote data storage solutions such as a server, mainframe, database or cloud services, distributed database or other suitable data storage solutions or any combination thereof. In some embodiments, the storage 104 may include, e.g., a suitable non-transient computer readable medium such as, e.g., random access memory (RAM), read only memory (ROM), one or more buffers and/or caches, among other memory devices or any combination thereof.

In some embodiments, the disease classification recommendation system 100 may implement computer engines for the NLP model(s) 110. In some embodiments, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, to parse the patient data 170 and produce a recommendation, the disease classification recommendation system 100 may include computer engines including the NLP model(s) 110. In some embodiments, the NLP model(s) 110 may include dedicated and/or shared software components, hardware components, or a combination thereof. For example, the NLP model(s) 110 may include a dedicated processor and storage. However, in some embodiments, the NLP model(s) 110 may share hardware resources, including the processor 102 and data store 104 of the disease classification recommendation system 100 via, e.g., a bus.

In some embodiments, the NLP model(s) 110 may include one or more algorithms to extract terminology relevant to a disease or condition, and analyze the identified terminology to determine a most likely classification of the disease or condition. In some embodiments, the terminology deemed relevant may be based on a set of learned terms, e.g., maintained in a dictionary 160. In some embodiments, the dictionary 160 may include terminology categorized according to disease/condition and associate classes thereof, such as mechanisms, types, severity, etc. Accordingly, the NLP model(s) 110 may access and/or query disease/condition specific terminology, including class-specific subsets of the disease/condition specific terminology so as to recognize occurrences of the terminology in the patient data 170.

In some embodiments, the dictionary 160 may include human curated, such as expert curated, terminology. For example, the terminology may be curated by one or more doctors that specialize in the associated disease/condition. Alternatively or in addition, the dictionary 160 may include machine learned terminology. For example, the dictionary 160 may include terms identified by one or more machine learning models based on scientific literature, supervised learning using historical patient data and known recommendations, or by any other technique or any combination thereof.

In some embodiments, the one or more machine learning models for curating the dictionary 160 may be configured to utilize one or more exemplary AI/machine learning techniques chosen from, but not limited to, decision trees, boosting, support-vector machines, neural networks, nearest neighbor algorithms, Naive Bayes, bagging, random forests, and the like. In some embodiments and, optionally, in combination of any embodiment described above or below, an exemplary neural network technique may be one of, without limitation, feedforward neural network, radial basis function network, recurrent neural network, convolutional network (e.g., U-net) or other suitable network. In some embodiments and, optionally, in combination of any embodiment described above or below, an exemplary implementation of Neural Network may be executed as follows:

a. define Neural Network architecture/model,
   b. transfer the input data to the exemplary neural network model, c. train the exemplary model incrementally,
   d. determine the accuracy for a specific number of timesteps,
   e. apply the exemplary trained model to process the newly received input data,
   f. optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values/functions and/or aggregation functions. For example, an activation function of a node may be a step function, sine function, continuous or piecewise linear function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

In some embodiments, the occurrences of the terminology may be analyzed based on classification parameters 150. In some embodiments, the classification parameters 150 may define how the NLP model(s) 110 weight and/or score occurrences of each term in the terminology, and based on such weighting/scoring, how the NLP model(s) 110 aggregate the weights and/or scores to create the classification recommendation 180.

In some embodiments, the classification parameters 150 may score each classification associated with a particular disease/condition of a particular patient. Based on the score of each classification, the classification parameters 150 may define how to combine the score of each classification to determine the classification recommendation 180. In some embodiments, the score of each classification may be based on whether the relevant terminology associated with each classification occurs, how many times relevant terminology occurs for each classification, how to weight each term that occurs, how to incorporate physiological and/or test measurements, among other factors or any combination thereof.

In some embodiments, the classification parameters 150 may include predefined logic, statistical modeling, machine learning techniques, among other techniques or any combination thereof. In some embodiments, the classification parameters 150 may be human curated, such as expert curated logic. For example, the parameters may be curated by one or more doctors that specialize in the associated disease/condition. Alternatively or in addition, the classification parameters 150 may include machine learned parameters. For example, the classification parameters 150 may include rules identified by one or more machine learning models based on scientific literature, supervised learning using historical patient data and known recommendations, or by any other technique or any combination thereof.

In some embodiments, when patient data 170 is obtained for a particular patient, the disease classification recommendation system 100 may use the NLP model(s) 110 to analyze the patient data 170 according to the dictionary 160 and classification parameters 150. Based on the dictionary 160 and classification parameters 150, the NLP model(s) 110 may produce the classification recommendation 180. The classification recommendation 180 may represent a recommendation to a doctor, nurse or the patient for a most likely class of the disease/condition associated with the patient based on the patient data 170. In some embodiments, the disease classification recommendation system 100 may provide the classification recommendation 180 to a user computing device 190. In some embodiments, the classification recommendation 180 may be appended to a patient's data 170, presented in a dashboard associated with a particular patient, presented in a list of patients to enable filtering based on the disease/condition and/or classes thereof, among other forms of presentation and representation or any combination thereof.

In some embodiments, the user may include any suitable healthcare professional qualified to review and assess the classification recommendation 180 and use the classification recommendation 180 as clinical decision support.

Figure 2:
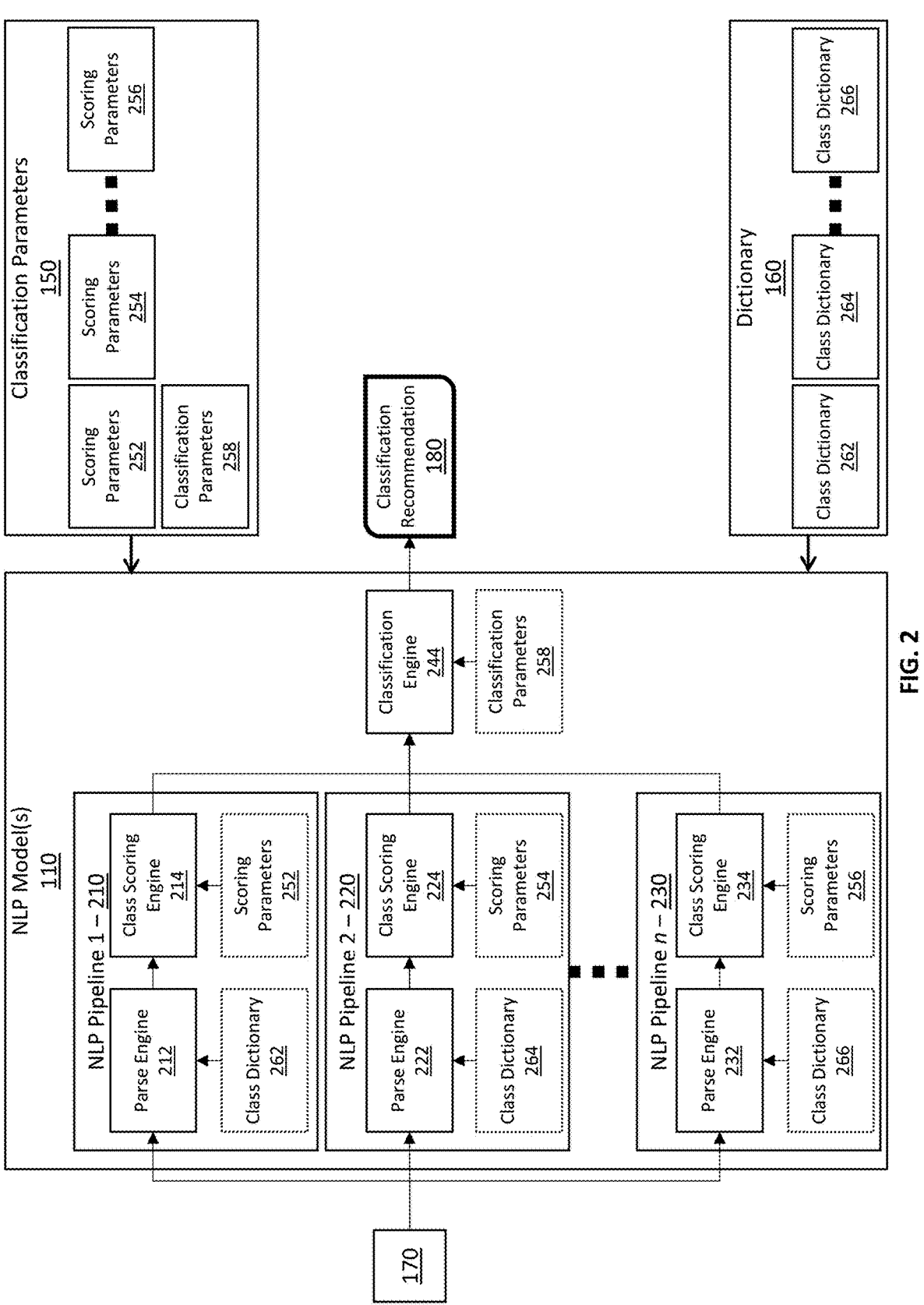
FIG. 2 depicts a NLP model to recommend a patient classification regarding one or more diagnoses in medical reports at scale in accordance with one or more embodiments of the present disclosure.

Referring to FIG. 2, an NLP model to recommend a patient classification regarding one or more diagnoses in medical reports at scale is depicted in accordance with one or more embodiments of the present disclosure.

In some embodiments, the NLP model(s) 110 may include multiple NLP pipelines, including NLP pipeline 1 210, NLP pipeline 2 220 through n 230 (collectively "the NLP pipelines 210-230"). The number of NLP pipelines 210-230 may depend on the disease/condition being tested. In some embodiments, the NLP model(s) 110 may implement an NLP pipeline for each category associated with the disease/condition being tested. For example, for a disease having four sub-types, the NLP model(s) 110 may include four NLP pipelines corresponding to the four sub-types such that each NLP pipeline generates a score for a respective sub-type of the disease. In some embodiments, the NLP model(s) 110 may be configured with any number of NLP pipelines 210-230 so as to generate a classification recommendation 180 for a disease/condition having any number of classes, including sub-types, severity classifications, mechanisms, or other categorizations of the disease/condition. For example, the NLP model(s) 110 can include 1, 2, 3, 4, 5, 6, 7, 8, 9, 10 or more NLP pipelines 210-230 depending on the number of classes.

In some embodiments, the NLP pipelines 210-230 may be configurable with classification parameters 150 and the dictionary 160 for the disease/classification. A particular category associated with a respective NLP pipeline 210-230 may have a particular set of terms that are indicative of that category for the disease/condition. Accordingly, each NLP pipeline 210-230 may include a respective parse engine 212, 222 through 232 that is configured to parse the patient data based on the terms of the corresponding class. Thus, for a category 1 of the disease/condition, the NLP pipeline 1 210 may include a parse engine 212 for parsing the patient data 170 to identify and analyze the terms indicative of category 1. Similarly, for a category 2 of the disease/condition, the NLP pipeline 2 220 may include a parse engine 222 for parsing the patient data 170 to identify and analyze the terms indicative of category 2, and for a category n of the disease/condition, the NLP pipeline n 230 may include a parse engine 232 for parsing the patient data 170 to identify and analyze the terms indicative of category n.

In some embodiments, the NLP model(s) 110 may utilize the dictionary 160 to configure each parse engine 212-232 with the class-specific dictionary 262, category-specific dictionary 264, through category-specific dictionary 266. Thus, the NLP model(s) 110 may access and/or import the category dictionary 262 to configure the parse engine 212 of the NLP pipeline 1 210, the category dictionary 264 to configure the parse engine 222 of the NLP pipeline 2 220, through the category dictionary 266 to configure the parse engine 232 of the NLP pipeline n 230. Each category dictionary 262-266 may establish the terminology of the corresponding category of the disease/condition. As such, the respective parse engines 212-232 may use each category dictionary 262-266 to structure queries of the patient data 170 to identify occurrences of the terminology.

In some embodiments, the dictionaries in dictionary 160 used to configure each parse engine for NLP model(s) 110 may include a customized tokenization function. In some embodiments, the tokenization function takes as input an input text such as the doctor's report in the patient data 170, and outputs a set of tokens representative of terms and/or phrases to capture concepts present in the input text. Similarly, the descriptors of interest for the category diction 262-266 may be represented as tokens or combinations thereof. Using NLP-based parsing, each word/phrase in the input text may be parsed and tokenized to identify the occurrence of both the verbatim terminology and equivalents such as changes in tense or gender, common spelling variations, among other variations to the terminology.

In some embodiments, the term "parse" or "parsing" refers to the process of analyzing a sentence, breaking it down into smaller components, and identifying the grammatical structure of the sentence to analyze a sentence's syntax and its underlying structure to extract meaning from it, thus enabling machines to understand human language. Based on the parsing of the terminology, the customized tokenization function may tokenize the descriptors for each category of the disease/condition.

In some embodiments, tokenization may include of 3 or more layers, including (1) parsing of individual words, (2) parsing word patterns with wildcard placements (e.g., pre-defined wildcard placements) that permit any token or word, and (3) parsing complete phrases verbatim. In some embodiments, parsing the individual words may include parsing all words/phrases, parsing words/phrases that match a valid descriptor per the customized tokenization function, or a combination thereof. In some embodiments, parsing the word patterns may include identifying word patterns that are within a discrete phrase and/or sentence, e.g., as demarcated by punctuation marks and/or other structures/characters or any combination thereof.

In some embodiments, the tokenization function segments unstructured text and natural language data into discrete elements using combinations of tokens, each representing a set of unique terms, plus additional words or complete phrases that are indicative of a relevant characteristic of the patient, resulting in a data structure that accounts for relevant vocabulary, abbreviations, negations, common variations in spelling, and combinations of words of phrases that are present in the patient data.

In some embodiments, based on the occurrences identified by the parse engines 212-232, respective category scoring engines 214, 224 through 234 may analyze the terminology to generate a score associated with each class.

To do so, the NLP pipelines 210-230 may be configurable with the classification parameters 150 for the disease/classification. In some embodiments, the classification parameters 150 may include scoring parameters 252, 254 through 256 corresponding to category scoring engines 214, 224 through 234 of the NLP pipelines 210, 220 through n 230, respectively. In some embodiments, the scoring parameters 252, 254 through 256 define the parameters for generating a score for a particular category based on the occurrences of particular terminology in the patient data 170.

In some embodiments, the scoring parameters 252-256 may include a definition of weightings for each term, each class, weighting of compounded terms or combinations of terms, weighting based on frequency of a given term or terms for a given class, among other weightings or any combination thereof. In some embodiments, the scoring parameters 252-256 may include scoring rules that define how a class-specific score is modulated based on one or more different triggers. For example, where one term has a first weighting and another term has a different weighting, the scoring parameters 252-256 may define a scoring rule that discards one or the other of the terms and only using the weighting of the non-discarded term.

In some embodiments, the scoring parameters 252-256 may weight terminology using integer values, decimal values, fractions or other numerical based on relevance to the associated class. In some embodiments, the numerical-based weighting may be on a spectrum of 0 to 1, 0 to 3, 0 to 5, 0 to 10, 1 to 3, 1 to 5, 1 to 10, or other scale or any combination thereof. In some embodiments, the scoring parameters 252-256 may weight terminology using categorical weights, such as tier 1, tier 2, tier 3, etc., high, medium, low, or other categorical demarcation based on relevance to the associated class. In some embodiments, the categorical-based weighting thus define, for each term, a categorical weighting.

In some embodiments, the scoring parameters 252-256 may establish scoring rules that defines how to aggregate the weightings of the terminology identified in the patient data 170. For example, the scoring parameters 252-256 may establish rules that define an algorithm for calculating a score based on each identified term, the weighting of the term, the frequency of occurrence of the term, a location in the patient data 170 (e.g., report body, diagnosis, doctor notes, etc.) of each occurrence, among other characteristics of each occurrence of the terminology or any combination thereof.

In some embodiments, the scoring parameters 252-256 may establish scoring rules that defines logical rules for selecting a score based on a highest or lowest weighting of the terminology occurring in the patient data 170. For example, the scoring parameters 252-256 may establish rules that define a selection methodology for calculating a score based on the most relevant terms according to the numerical and/or categorical weightings, the frequency of occurrence of the most relevant terms, a location in the patient data 170 (e.g., report body, diagnosis, doctor notes, etc.) of the most relevant terms, among other characteristics of each occurrence of the terminology or any combination thereof. For example, the rules may define that the score is calculated as the weighting of highest weighted term that occurs in the patient data 170, or is based on the frequency of the highest weighted term that occurs in the patient data 170. In another example, the rules may define that the score is calculated as the weighting of the most frequent term that occurs in the patient data 170, or is based on the weighting of the most frequent term that occurs in the patient data 170.

In some embodiments, the scoring parameters 252-256 may establish scoring rules that defines a combination of algorithm(s) and/or logical rule(s) to calculate the final score for a given category based on the terminology of the class. Thus, using the scoring parameters 252-256, the category scoring engine 214 may output a score indicative of a likelihood of the category being applicable to the disease/condition based on the identified terminology by the parse engine 212-232.

In some embodiments, the score for each category produced by each NLP pipeline 210-230 may be analyzed by a classification engine 244 to produce the classification recommendation 180. Thus, based on the scores, the classification engine 244 may select a category that is most likely applicable to the disease/condition.

In some embodiments, the classification engine 244 may employ classification parameters 258 of the classification parameters 150. In some embodiments, the classification parameters 258 may define how to balance, weight or otherwise reconcile the class-specific scores produced by the NLP pipelines 210-230. For example, the classification parameters 258 may select the category having the highest score. In some embodiments, the classification parameters 258 may apply class-specific weights, such that the score produced by each NLP pipeline 210-230 is modified with a class-specific weight. Upon weighting, the classification parameters 258 may configure the classification engine 244 to select the highest modified score after applying the class-specific weightings.

In some embodiments, the classification parameters 258 may configure the classification engine 244 to apply a tiebreaker where two or more scores are the same or substantially similar. In some embodiments, the tiebreaker may include a test result or physiological measurement associated with the presence or absence of a particular category of the disease/condition. For example, a prostate-specific antigen (PSA) level may be used as a tiebreaker for malignant or benign prostate cancer, or an ejection fraction (EF) value may be used as a tiebreaker for primary degenerative or secondary mitral regurgitation (MR).

In some embodiments, the custom tokenization function of the dictionary 160 may segment the available unstructured text and natural language data using a total set of over 200 combinations of 37 tokens (representing a total of over 3,000 unique terms), plus additional words or complete phrases that are indicative of a relevant characteristic of the patient, to accurately identify the relevant descriptors of the mechanism of MR while accounting for relevant vocabulary, abbreviations, negations, common variations in spelling, and combinations of words or phrases that are present in the patient data. In some embodiments, the combinations of tokens and/or the tokens themselves may be hand-crafted (e.g., produced manually), or may be automatically generated using one or more tokenizations functions and/or NLP models (e.g., machine learning-based NLP models), or other tokenization technique or any combination thereof. For example, the machine learning-based NLP model(s) may include one or more supervised and/or unsupervised machine learning models trained on, e.g., scientific literature, historical written reports, or other training set or any combination thereof.

In some embodiments, an example of a tokenized set relevant to primary degenerative MR descriptors may include the following (where " . . . " would indicate a wildcard, would indicate tokenized derivatives, "{ }" would indicate a sentence or other standalone line of text demarcated by relevant punctuation marks, and "~~" would indicate a negation):

| a. | {primary secondary type <<mv>>} |
|----|----|
| b. | {<<mv>> primary secondary type} |
| c. | {<<mv>> ... <<primary>>} |
| d. | {<<primary>> ... <<mv>>} |
| e. | ~~primary MR orifice |
| f. | ~~primary orifice |
| g. | ~~primary jet |
| h. | ~~primary of |
| i. | {<<mv>> ... <<degenerative>>} |
| j. | {<<degenerative>> ... <<mv>>} |
| k. | ~~{<<not>> ... <<mv>> ... <<prolapse>>} |
| l. | ~~mitral valve without significant stenosis or prolapse |
| m. | ~~{<<mv>> ... <<not>> ... <<prolapse>>} |
| n. | {<<mv>> ... <<prolapse>>} |
| o. | {<<prolapse>> ... <<mv>>} |
| p. | ~~<<not>> ... <<mv>> ... <<flail>> |
| q. | ~~{<<mv>> ... <<not>> ... <<flail>>} |
| r. | ~~{<<not>> ... <<flail>> ... <<mv>>} |
| s. | ~~{<<mv>> ... <<not>> ... <<not>> <<flail>>} |
| t. | {<<mv>> ... <<flail>>} |
| u. | {<<flail>> ... <<mv>>} |
| v. | {<<myxomatous>> ... <<mv>>} |
| w. | {<<mv>> ... <<myxomatous>>} |
| x. | <<barlow>> |
| y. | {<<mv>> ... <<ruptured>> ... <<chord>>} |
| z. | {<<ruptured>> ... <<mv>> ... <<chord>>} |
| aa. | {<<ruptured>> ... <<chord>> ... <<mv>>} |
| bb. | {<<mv>> ... <<chord>> ... <<ruptured>>} |
| cc. | {<<chord>> ... <<mv>> ... <<ruptured>>} |
| dd. | {<<chord>> ... <<ruptured>> ... <<mv>>} |
| ee. | <<fibroelasticity>> |

As a result, in some embodiments, the classification engine 244 may be configured according to the classification parameters 258 to output a particular category as the classification recommendation 180. Thus, the NLP model(s) 110 may recommend a disease/condition recommendation to a user to assist in informing treatment, trial enrollment eligibility, among other patient interactions or any combination thereof.

Figure 3:
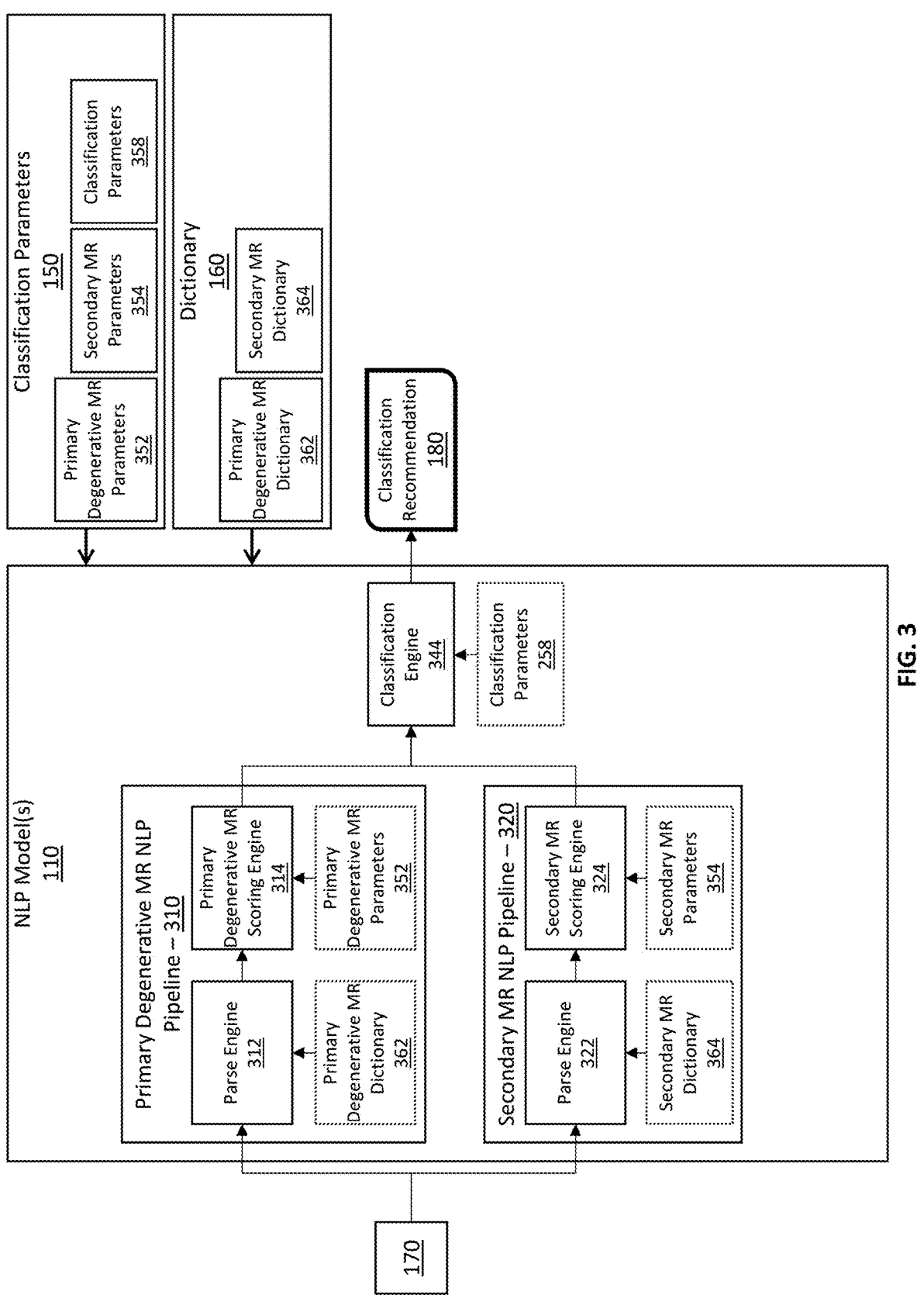
FIG. 3 depicts an exemplary NLP model to recommend a patient classification regarding one or more mechanisms of MR in echocardiographic reports at scale in accordance with one or more embodiments of the present disclosure.

Referring to FIG. 3, an exemplary NLP model to recommend a patient classification regarding one or more mechanisms of MR in echocardiographic reports at scale is depicted in accordance with one or more embodiments of the present disclosure.

In some embodiments, mitral regurgitation (MR) is highly prevalent both in the US and worldwide and is an important determinant of morbidity and mortality. The mechanisms of MR are divided broadly as primary and secondary: in primary MR the main abnormality affects the valve, the most important subset of which is degenerative (e.g., mitral prolapse and flail). Herein, the term "primary degenerative" refers to a type of MR under consideration from a treatment perspective (e.g., rheumatic mitral valve disease is considered relatively less suitable for repair), while the term "secondary (or functional)" MR refers to the abnormality being present in other structures such as the left ventricle or atrium. In some embodiments, mixed MR occurs when primary and secondary mechanisms co-exist. Since clinical guideline recommendations for therapeutic options and expected patient outcomes differ by mechanism, proper identification and description of the mechanism of MR is essential to patient care and treatment decisions.

In some embodiments, doppler echocardiography may provide the evaluation of valvular regurgitation, and clinician-determined findings may be documented in the patient data 170, such as in the text of echocardiographic reports. In some embodiments, to identify in the patient data 170 indications of primary degenerative, secondary or mixed MR, the NLP model(s) 110 may be configured for identification of relevant descriptors of the mechanism(s) of MR per clinical guidelines by leveraging an extensive database of echocardiographic report data.

In some embodiments, the NLP model(s) 110 may identify descriptors of the mechanism(s) of MR (whether primary degenerative or secondary; see Table 1). Because clinicians may inconsistently describe their findings related to MR in a patient, simple keyword searching for "primary degenerative," "secondary" or "mixed" may be unreliable is interpreting the clinician's assessment. Thus, the descriptors may include terminology and phrases that suggest or indicate which mechanism is associated with the patient's disease. In some embodiments, the NLP model(s) 110 may then use a rules-based framework to sort echocardiographic reports of MR according to a clinician-defined rules set, which allocates the descriptors identified by NLP in a tiered hierarchy of higher-versus lower-confidence categories (see, for example, FIGS. 4 and 5) to enable efficient, pragmatic sorting of MR diagnoses as likely primary degenerative/secondary/mixed at scale, whether for secondary clinical review or research purposes.

In some embodiments, to enable the NLP model(s) 110 to generate a classification recommendation 180 of primary degenerative, secondary or mixed MR for a given patient, the NLP model(s) 110 may include two NLP pipelines, a primary degenerative MR NLP pipeline 310 and a secondary MR NLP pipeline 320. In some embodiments, the NLP pipelines 310 and 320 may be configurable with classification parameters 150 and the dictionary 160 for the disease/classification. Primary degenerative MR may have a particular set of terms that are indicative of primary degenerative MR, while secondary MR may have a particular set of terms that are indicative of secondary MR. Accordingly, each NLP pipeline 310 and 320 may include a respective parse engine 312 and 322 that is configured to parse the patient data based on the terms of the corresponding mechanism of MR. Thus, for primary degenerative MR, the primary degenerative MR NLP pipeline 310 may include a parse engine 312 for parsing the patient data 170 to identify and analyze the terms indicative of primary degenerative MR. Similarly, for secondary MR, the secondary MR NLP pipeline 320 may include a parse engine 322 for parsing the patient data 170 to identify and analyze the terms indicative of secondary MR.

In some embodiments, the NLP model(s) 110 may utilize the dictionary 160 to configure each parse engine 312 and 322 with the primary degenerative MR dictionary 362 and secondary MR dictionary 364. Thus, the NLP model(s) 110 may access and/or import the primary degenerative MR dictionary 362 to configure the parse engine 312 of the primary degenerative MR NLP pipeline 310 and the secondary MR dictionary 364 to configure the parse engine 322 of the secondary MR NLP pipeline 320. Each category dictionary 362 and 364 may establish the terminology of the corresponding mechanism of MR, as detailed further below. As such, the respective parse engines 312 and 322 may use each dictionary 362 and 364 to structure queries of the patient data 170 to identify occurrences of the terminology.

In some embodiments, based on the occurrences identified by the parse engines 312 and 322, the primary degenerative MR scoring engine 314 and the secondary MR scoring engine 324 may analyze the terminology to generate a score associated with each mechanism of MR. To do so, the NLP pipelines 310 and 320 may be configurable with the classification parameters 150 for the MR. In some embodiments, the classification parameters 150 may include primary degenerative MR parameters 352 and secondary MR parameters 354 corresponding to the primary degenerative MR scoring engine 314 and the secondary MR scoring engine 324, respectively.

In some embodiments, each of the primary degenerative MR parameters 352 and the secondary MR parameters 354 may weight terminology using categorical weights, such as tier 1, tier 2, tier 3, etc., high, medium, low, or other categorical demarcation based on relevance to the associated class. In some embodiments, the categorical-based weighting thus define, for each term, a categorical weighting of how strongly each descriptor indicates primary degenerative or secondary MR.

In some embodiments, the primary degenerative MR parameters 352 and the secondary MR parameters 354 may establish scoring rules that define logical rules for selecting an indicator of likelihood of primary degenerative and secondary MR, respectively, based on a highest or lowest weighting of the terminology occurring in the patient data 170. In some embodiments, as illustrated in FIGS. 4 and 5 detailed below, each descriptor may be assigned a Tier 1, Tier 2 or Tier 3 category. Thus, for primary degenerative MR, the primary degenerative MR NLP pipeline 310, upon identifying occurrences of descriptions set forth in the primary degenerative MR dictionary 362, may determine a score indicative of likelihood of primary degenerative MR based on the highest tier descriptor identified. Thus, if the parse engine 312 identifies a Tier 1 descriptor, the primary degenerative MR scoring engine 314 produces a Tier 1 score even where a larger number of Tier 2 and/or Tier 3 descriptors are also identified. Similarly, for secondary MR, the secondary MR NLP pipeline 320, upon identifying occurrences of descriptions set forth in the secondary MR dictionary 364, may determine a score indicative of likelihood of secondary MR based on the highest tier descriptor identified. Thus, if the parse engine 322 identifies a Tier 1 descriptor, the secondary MR scoring engine 324 produces a Tier 1 score even where a larger number of Tier 2 and/or Tier 3 descriptors are also identified. However, as detailed above, other scoring methodologies may be implemented.

In some embodiments, the score for primary degenerative MR and for secondary MR produced by each NLP pipeline 310 and 320 may be analyzed by a classification engine 344 to produce the classification recommendation 180. Thus, based on the scores, the classification engine 344 may select primary degenerative MR, secondary MR or a combination thereof, e.g., "mixed," that is most likely applicable to MR.

In some embodiments, the classification engine 344 may employ classification parameters 358 of the classification parameters 150. In some embodiments, the classification parameters 358 may define how to balance, weight, or otherwise reconcile the class-specific scores produced by the NLP pipelines 310 and 320. For example, as illustrated in example scoring and classification parameters of FIGS. 4 and 5, the classification parameters 358 may select primary degenerative, secondary or mixed MR based on the Tier of the descriptors of each of primary degenerative and secondary MR.

In some embodiments, the classification parameters 358 may configure the classification engine 344 to apply a tiebreaker where two or more scores are the same or substantially similar, such as where both primary degenerative and secondary MR have Tier 2 and/or Tier 3 scores as exemplified in FIGS. 4 and 5. In some embodiments, the tiebreaker may include a test result or physiological measurement associated with the presence or absence of a particular category of MR. For example, an EF value may be used as a tiebreaker for primary degenerative or secondary MR.

In some embodiments, where the score of each of primary degenerative and secondary MR are sufficiently low, e.g., Tier 3 or absent any descriptors at all, the classification parameters 358 may configure the classification engine 344 to apply an "unknown" classification that indicates an inability to make a determination.

As a result, in some embodiments, the classification engine 344 may be configured according to the classification parameters 358 to output a particular category as the classification recommendation 180 including "primary degenerative MR", "secondary MR", "mixed MR" or unknown. Thus, the NLP model(s) 110 may recommend an MR mechanism recommendation to a user to support clinical decisions regarding treatment, trial enrollment eligibility, among other patient interactions or any combination thereof.

In some embodiments, the NLP model(s) 110 may be informed by study of 300 randomly selected, deidentified echocardiographic reports with documented MR of moderate or greater severity, and then tested/validated using a fully independent random sample of 300 deidentified reports. In such study, the NLP model(s) 110 found to sort reports with an accuracy of at least 97% (per adjudication by manual review against the clinician-defined rules framework; see Table 2). For example, the NLP model(s) 110 may be tested via application to a deidentified research dataset of 183,321 echocardiographic reports generated between 2018 and 2023 from 25 US institutions with appropriate data permissions. In such a test, the reports may include a diagnosis of MR of moderate or greater severity (as identified via a separate validated NLP-based algorithm; validation findings summarized in Table 3).

TABLE 1

| Clinician-defined eligible descriptor categories for primary degenerative and secondary mitral regurgitation. | |
| --- | --- |
| Primary degenerative MR descriptor concepts | Secondary (functional) MR descriptor concepts |
| Primary | Secondary |
| Degenerative | Ischemic |
| Prolapse | Functional |
| Flail | Leaflet tethering/restriction |
| Myxomatous | Left ventricular dilation |
| Barlow's | Left ventricular systolic dysfunction |
| Ruptured chord(ae) | Dilated cardiomyopathy |
| Fibroelastic (deficiency) | Ischemic cardiomyopathy |
| Leaflet calcification | Central mitral regurgitation |
| Leaflet thickening | Annular dilation |
| Valve thickening | Left atrial dilation |
| Mitral cleft | |
| Annular calcification | |

MR, mitral regurgitation.

TABLE 2

| Performance of NLP-based algorithm to identify mechanism of MR. | |
| --- | --- |
| Algorithm type | Accuracy, % |
| Maximal (population capture) | 97.3 |
| Minimal (highest-confidence capture) | 99.0 |

[a]As assessed via a random fully deidentified independent validation dataset of n = 300 echocardiographic reports
MR, mitral regurgitation; NLP, NLP.

TABLE 3

Performance of algorithm to identify diagnosed MR severity.

| Category[a] | Accuracy, % |
|---|---|
| No diagnosis found | 100.0 |
| Indeterminate severity | 98.5 |
| None | 100.0 |
| Mild | 100.0 |
| Mild-to-moderate | 100.0 |
| Moderate | 100.0 |

TABLE 3-continued

Performance of algorithm to identify diagnosed MR severity.

| Category[a] | Accuracy, % |
|---|---|
| Moderate-to-severe | 100.0 |
| Severe | 100.0 |

[a]As assessed via random deidentified sampling exercise of n = 200 echocardiographic reports per labeling category
MR, mitral regurgitation; NLP.

TABLE 4

Summary of insights derived from NLP-based algorithm and clinician-defined framework for the entire dataset.

| Descriptor analysis | Relative prevalence in reports of ≥moderate MR (N = 183,321),[a] n, % | Relative prevalence in reports of severe MR only (N = 28,317),[a] n, % |
|---|---|---|
| Any descriptor of MR mechanism | 173,471 (94.6%) | 27,518 (97.2%) |
| Any high-confidence descriptor of MR mechanism | 33,874 (18.5%) | 12,215 (43.1%) |
| Any primary degenerative MR descriptor | 139,359 (76.0%) | 23,386 (82.6%) |
| Any high-confidence primary degenerative MR descriptor | 28,192 (15.4%) | 10,390 (36.7%) |
| Any secondary MR descriptor | 140,702 (76.8%) | 23,305 (82.3%) |
| Any high-confidence secondary MR descriptor | 6,491 (3.5%) | 2,273 (8.0%) |
| Primary degenerative MR descriptors High-confidence descriptor set | | |
| Primary | 1,913 (1.0%) | 1,205 (4.3%) |
| Degenerative | 0 (0.0%) | 0 (0.0%) |
| Prolapse | 14,200 (7.7%) | 4,300 (15.2%) |
| Flail | 1,361 (0.7%) | 1,059 (3.7%) |
| Myxomatous | 9,650 (5.3%) | 3,120 (11.0%) |
| Barlow's | 164 (0.1%) | 116 (0.4%) |
| Ruptured chord(ae) | 884 (0.5%) | 580 (2.0%) |
| Fibroelastic (deficiency) | 20 (<0.1%) | 10 (<0.1%) |
| Leaflet calcification, ≥moderate | 4,263 (2.3%) | 535 (1.9%) |
| Leaflet thickening | 54,222 (29.6%) | 7,193 (25.4%) |
| Leaflet calcification, <moderate/unspecified | 3,263 (1.8%) | 368 (1.3%) |
| Valve thickening | 18,772 (10.2%) | 2,044 (7.2%) |
| Mitral cleft | 310 (0.2%) | 116 (0.4%) |
| Annular calcification | 30,337 (16.5%) | 2,740 (9.7%) |
| Secondary (functional) MR descriptors High-confidence descriptor set | | |
| Secondary | 3,289 (1.8%) | 1,341 (4.7%) |
| Ischemic | 0 (0.0%) | 0 (0.0%) |
| Functional | 3,202 (1.7%) | 932 (3.3%) |
| LV systolic dysfunction/ reduced LV systolic function, severe | 13,988 (7.6%) | 2,075 (7.3%) |
| LV systolic dysfunction/ reduced systolic function, <severe/unspecified | 13,469 (7.3%) | 1,377 (4.9%) |
| LV dilation/dilatation/ enlargement, severe | 6,841 (3.7%) | 1,669 (5.9%) |
| LV dilation/dilatation/ enlargement, <severe/unspecified | 18,279 (10.0%) | 3,398 (12.0%) |
| Leaflet tethering/restriction | 3,002 (1.6%) | 1,090 (3.8%) |
| Dilated cardiomyopathy | 34 (<0.1%) | 9 (<0.1%) |
| Ischemic cardiomyopathy | 318 (0.2%) | 26 (0.1%) |
| Central (mitral) regurgitation | 1,234 (0.7%) | 266 (0.9%) |
| Annular dilation/dilatation/ enlargement | 1,130 (0.6%) | 215 (0.8%) |
| LA dilation/dilatation/ enlargement | 75,916 (41.4%) | 10,907 (38.5%) |

TABLE 4-continued

Summary of insights derived from NLP-based algorithm and
clinician-defined framework for the entire dataset.

| Clinician-defined tiered rules framework analysis | Proportion of reports unsortable, % | Proportion of reports unsortable, % |
| --- | --- | --- |
| Minimal (highest-confidence capture only) descriptor framework | 77.4% | 52.7% |
| Maximal (population capture) framework | 50.7% | 31.8% |

[a]Proportions of reports (within this multicenter deidentified dataset) with a given descriptor labeled as the strongest leading descriptor of possible mechanism of MR.
LA, left atrial; LV, left ventricular; MR, mitral regurgitation; NLP, NLP.

In some embodiments, high-confidence descriptors of primary degenerative MR may include, e.g., primary, degenerative, prolapse, flail, myxomatous, Barlow's, ruptured chord[ae], fibroelastic [deficiency], among others. In some embodiments, the high-confidence ("Tier 1") descriptors were found in only 15.4% of cases (Table 4). High-confidence descriptors of secondary MR may include, e.g., secondary, ischemic, functional, among others. The high-confidence descriptors for secondary MR were found in 3.5% (Table 4). Overall, 81.5% were lacking any high-confidence descriptor (whether primary degenerative/secondary). When applying the complete rules-based framework, 77.4% were unsortable by mechanism per the clinician-defined rules leveraging that high-confidence descriptor set (FIG. 5 and Table 4). Even among those reporting severe MR, 52.7% still could not be sorted as primary degenerative/secondary/ mixed. After screening for multiple tiers of additional possible descriptors, 50.7% of reports of MR of moderate or greater severity and 31.8% of reports of severe MR were still unsortable (FIG. 4 and Table 4). Finally, 5.4% had no eligible descriptor of the mechanism of MR at all (Table 4).

Referring to FIG. 4, an illustrative maximal (population capture) clinician-defined tiered rules framework for NLP of diagnosed MR mechanism in echocardiographic reports at scale is depicted in accordance with one or more embodiments of the present disclosure.

Referring to FIG. 5, an illustrative minimal (highest-confidence capture only) clinician-defined tiered rules framework for NLP of diagnosed MR mechanism in echocardiographic reports at scale is depicted in accordance with one or more embodiments of the present disclosure.

Figure 6:
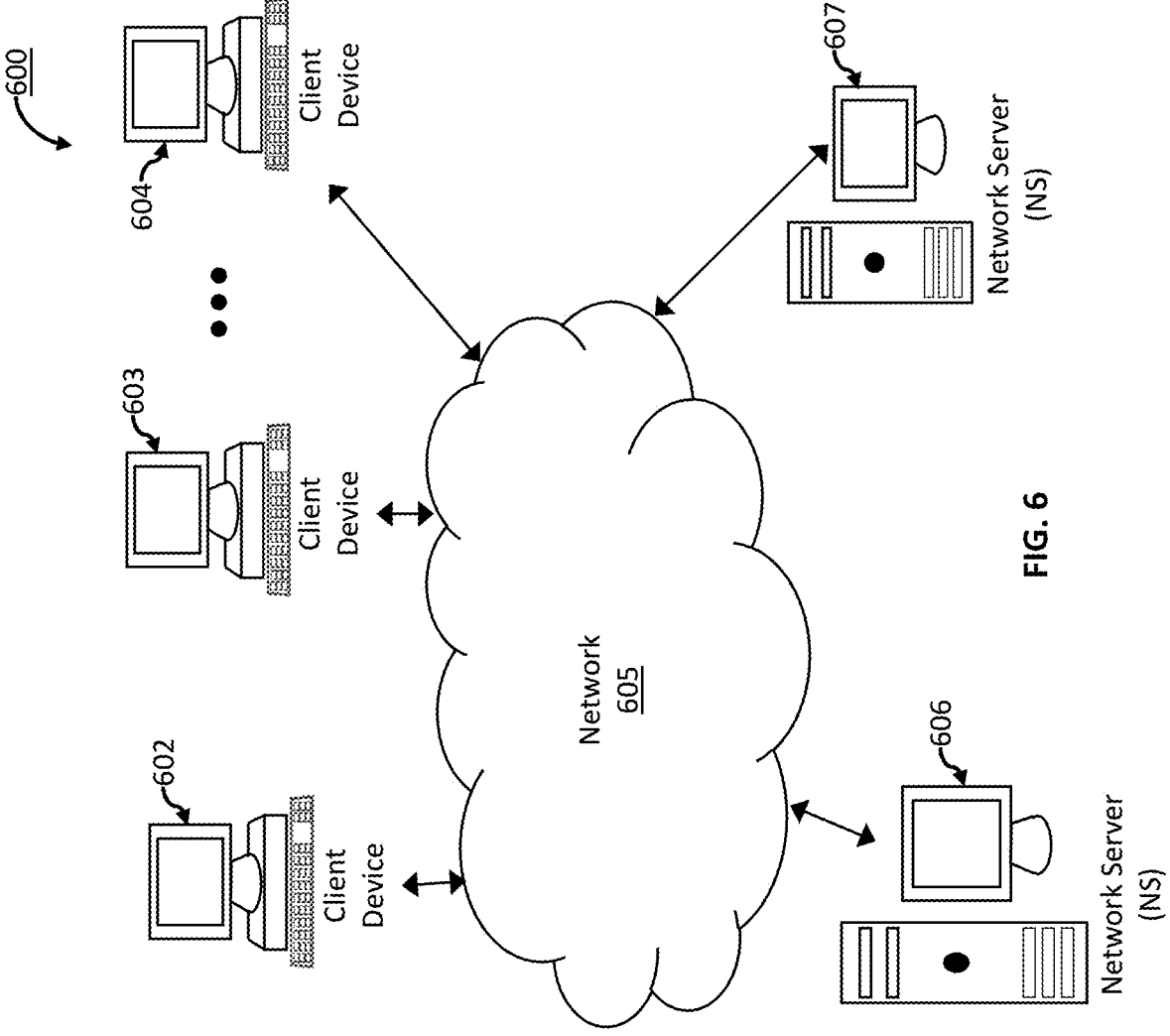
FIG. 6 depicts a block diagram of an exemplary computer-based system and platform for disease classification recommendation system in accordance with one or more embodiments of the present disclosure.

FIG. 6 depicts a block diagram of an exemplary computer-based system and platform 600 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the illustrative computing devices and the illustrative computing components of the exemplary computer-based system and platform 600 may be configured to manage a large number of members and concurrent transactions, as detailed herein. In some embodiments, the exemplary computer-based system and platform 600 may be based on a scalable computer and network architecture that incorporates varies strategies for assessing the data, caching, searching, and/or database connection pooling. An example of the scalable architecture is an architecture that is capable of operating multiple servers.

In some embodiments, referring to FIG. 6, client device 602, client device 603 through client device 604 (e.g., clients) of the exemplary computer-based system and platform 600 may include virtually any computing device capable of receiving and sending a message over a network (e.g., cloud network), such as network 605, to and from another computing device, such as servers 606 and 607, each other, and the like. In some embodiments, the client devices 602 through 604 may be personal computers, multiprocessor systems, microprocessor-based or programmable consumer electronics, network PCs, and the like. In some embodiments, one or more client devices within client devices 602 through 604 may include computing devices that typically connect using a wireless communications medium such as cell phones, smart phones, radio frequency (RF) devices, infrared (IR) devices, integrated devices combining one or more of the preceding devices, or virtually any mobile computing device, and the like. In some embodiments, one or more client devices within client devices 602 through 604 may be devices that are capable of connecting using a wired or wireless communication medium such as a PDA, POCKET PC, wearable computer, a laptop, tablet, desktop computer, a netbook, a video game device, a pager, a smart phone, an ultra-mobile personal computer (UMPC), and/or any other device that is equipped to communicate over a wired and/or wireless communication medium (e.g., NFC, RFID, NBIOT, 3G, 4G, 5G, GSM, GPRS, WiFi, WiMax, CDMA, OFDM, OFDMA, LTE, satellite, ZigBee, etc.). In some embodiments, one or more client devices within client devices 602 through 604 may include may run one or more applications, such as Internet browsers, mobile applications, voice calls, video games, videoconferencing, and email, among others. In some embodiments, one or more client devices within client devices 602 through 604 may be configured to receive and to send web pages, and the like. In some embodiments, an exemplary specifically programmed browser application of the present disclosure may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, a client device within client devices 602 through 604 may be specifically programmed by either Java, .Net, QT, C, C++, Python, PHP and/or other suitable programming language. In some embodiment of the device software, device control may be distributed between multiple standalone applications. In some embodiments, software components/applications can be updated and redeployed remotely as individual units or as a full software suite. In some embodiments, a client device may periodically report status or send alerts over text or email. In some embodiments, a client device may contain a data recorder which is remotely downloadable by the user using network protocols such as FTP, SSH, or other file transfer mechanisms. In some embodiments, a client device may provide several levels of user interface, for example, advance user, standard user. In some embodiments, one or more client devices within client devices 602 through 604 may be specifically programmed include or execute an application to perform a variety of possible tasks, such as, without limitation, messaging functionality, browsing, searching, playing, streaming or displaying various forms of content, including locally stored or uploaded messages, images and/or video, and/or games.

In some embodiments, the exemplary network 605 may provide network access, data transport and/or other services to any computing device coupled to it. In some embodiments, the exemplary network 605 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In some embodiments, the exemplary network 605 may implement one or more of a GSM architecture, a General Packet Radio Service (GPRS) architecture, a Universal Mobile Telecommunications System (UMTS) architecture, and an evolution of UMTS referred to as Long Term Evolution (LTE). In some embodiments, the exemplary network 605 may include and implement, as an alternative or in conjunction with one or more of the above, a WiMAX architecture defined by the WiMAX forum. In some embodiments and, optionally, in combination of any embodiment described above or below, the exemplary network 605 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 605 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMax, CDMA, OFDM, OFDMA, LTE, satellite and any combination thereof. In some embodiments, the exemplary network 605 may also include mass storage, such as network attached storage (NAS), a storage area network (SAN), a content delivery network (CDN) or other forms of computer or machine readable media.

In some embodiments, the exemplary server 606 or the exemplary server 607 may be a web server (or a series of servers) running a network operating system, examples of which may include but are not limited to Apache on Linux or Microsoft IIS (Internet Information Services). In some embodiments, the exemplary server 606 or the exemplary server 607 may be used for and/or provide cloud and/or network computing. Although not shown in FIG. 6, in some embodiments, the exemplary server 606 or the exemplary server 607 may have connections to external systems like email, SMS messaging, text messaging, ad content providers, etc. Any of the features of the exemplary server 606 may be also implemented in the exemplary server 607 and vice versa.

In some embodiments, one or more of the exemplary servers 606 and 607 may be specifically programmed to perform, in non-limiting example, as authentication servers, search servers, email servers, social networking services servers, Short Message Service (SMS) servers, Instant Messaging (IM) servers, Multimedia Messaging Service (MMS) servers, exchange servers, photo-sharing services servers, advertisement providing servers, financial/banking-related services servers, travel services servers, or any similarly suitable service-base servers for users of the client devices 602 through 604.

In some embodiments and, optionally, in combination of any embodiment described above or below, for example, one or more exemplary computing client devices 602 through 604, the exemplary server 606, and/or the exemplary server 607 may include a specifically programmed software module that may be configured to send, process, and receive information using a scripting language, a remote procedure call, an email, a tweet, Short Message Service (SMS), Multimedia Message Service (MMS), instant messaging (IM), an application programming interface, Simple Object Access Protocol (SOAP) methods, Common Object Request Broker Architecture (CORBA), HTTP (Hypertext Transfer Protocol), REST (Representational State Transfer), SOAP (Simple Object Transfer Protocol), MLLP (Minimum Lower Layer Protocol), or any combination thereof.

Figure 7:
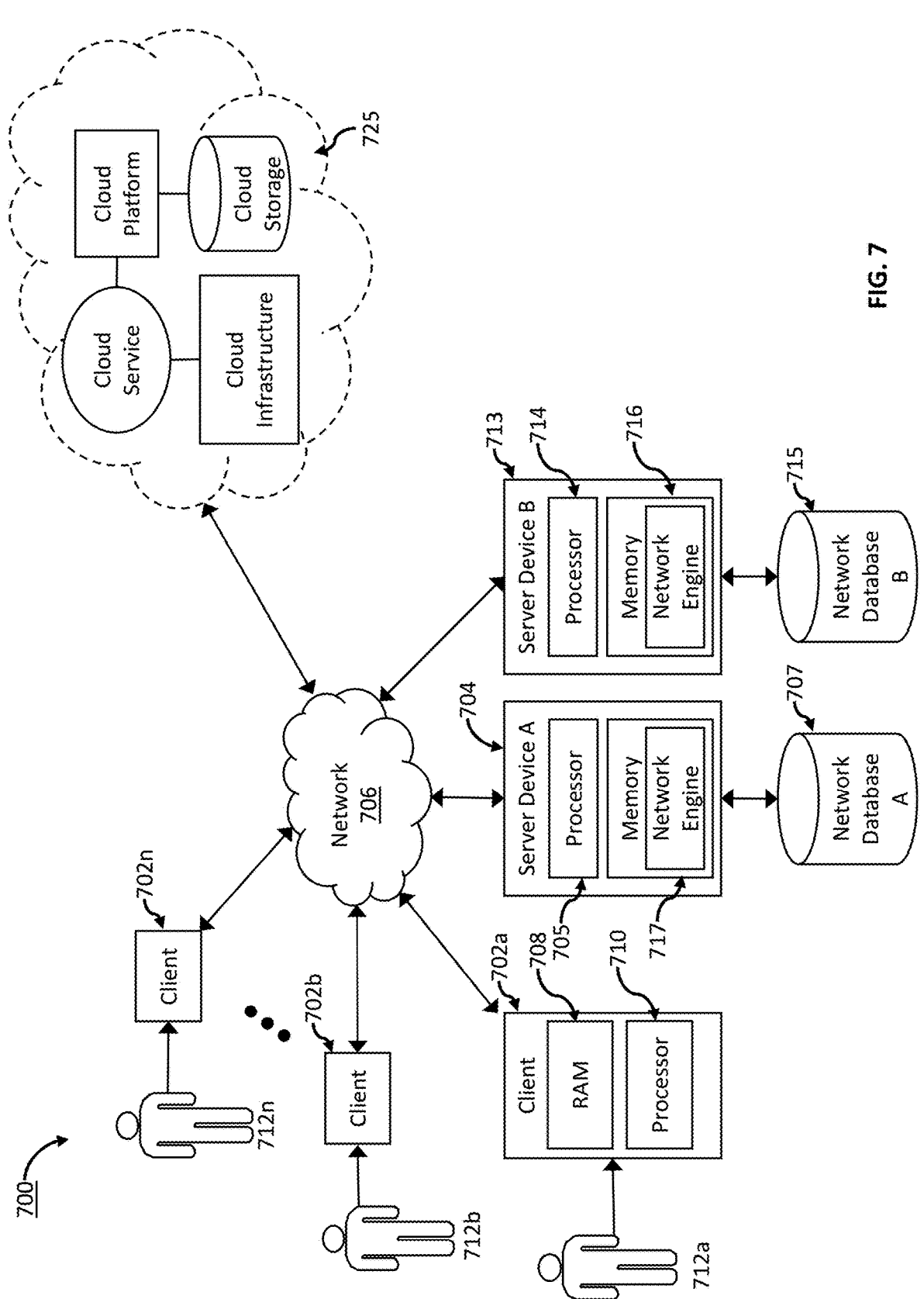
FIG. 7 depicts a block diagram of another exemplary computer-based system and platform for disease classification recommendation system in accordance with one or more embodiments of the present disclosure.

FIG. 7 depicts a block diagram of another exemplary computer-based system and platform 700 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the client device 702a, client device 702b through client device 702n shown each at least includes a computer-readable medium, such as a random-access memory (RAM) 708 coupled to a processor 710 or FLASH memory. In some embodiments, the processor 710 may execute computer-executable program instructions stored in memory 708. In some embodiments, the processor 710 may include a microprocessor, an ASIC, and/or a state machine. In some embodiments, the processor 710 may include, or may be in communication with, media, for example computer-readable media, which stores instructions that, when executed by the processor 710, may cause the processor 710 to perform one or more steps described herein. In some embodiments, examples of computer-readable media may include, but are not limited to, an electronic, optical, magnetic, or other storage or transmission device capable of providing a processor, such as the processor 710 of client device 702a, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, JavaScript, and etc.

In some embodiments, client devices 702a through 702n may also comprise a number of external or internal devices such as a mouse, a CD-ROM, DVD, a physical or virtual keyboard, a display, or other input or output devices. In some embodiments, examples of client devices 702a through 702n (e.g., clients) may be any type of processor-based platforms that are connected to a network 706 such as, without limitation, personal computers, digital assistants, personal digital assistants, smart phones, pagers, digital tablets, laptop computers, Internet appliances, and other processor-based devices. In some embodiments, client devices 702a through 702n may be specifically programmed with one or more application programs in accordance with one or more principles/methodologies detailed herein. In some embodiments, client devices 702a through 702n may operate on any operating system capable of supporting a browser or browser-enabled application, such as Microsoft™, Windows™, and/or Linux. In some embodiments, client devices 702a through 702n shown may include, for example, personal computers executing a browser application program such as Microsoft Corporation's Internet Explorer™, Apple Computer, Inc.'s Safari™, Mozilla Firefox, and/or Opera. In some embodiments, through the member computing client devices 702a through 702n, user 712a, user 712b through user 712n, may communicate over the exemplary network 706 with each other and/or with other systems and/or devices coupled to the network 706. As shown in FIG. 7, exemplary server devices 704 and 713 may include processor 705 and processor 714, respectively, as well as memory 717 and memory 716, respectively. In some embodiments, the server devices 704 and 713 may be also coupled to the network 706. In some embodiments, one or more client devices 702a through 702n may be mobile clients.

In some embodiments, at least one database of exemplary databases 707 and 715 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 8:
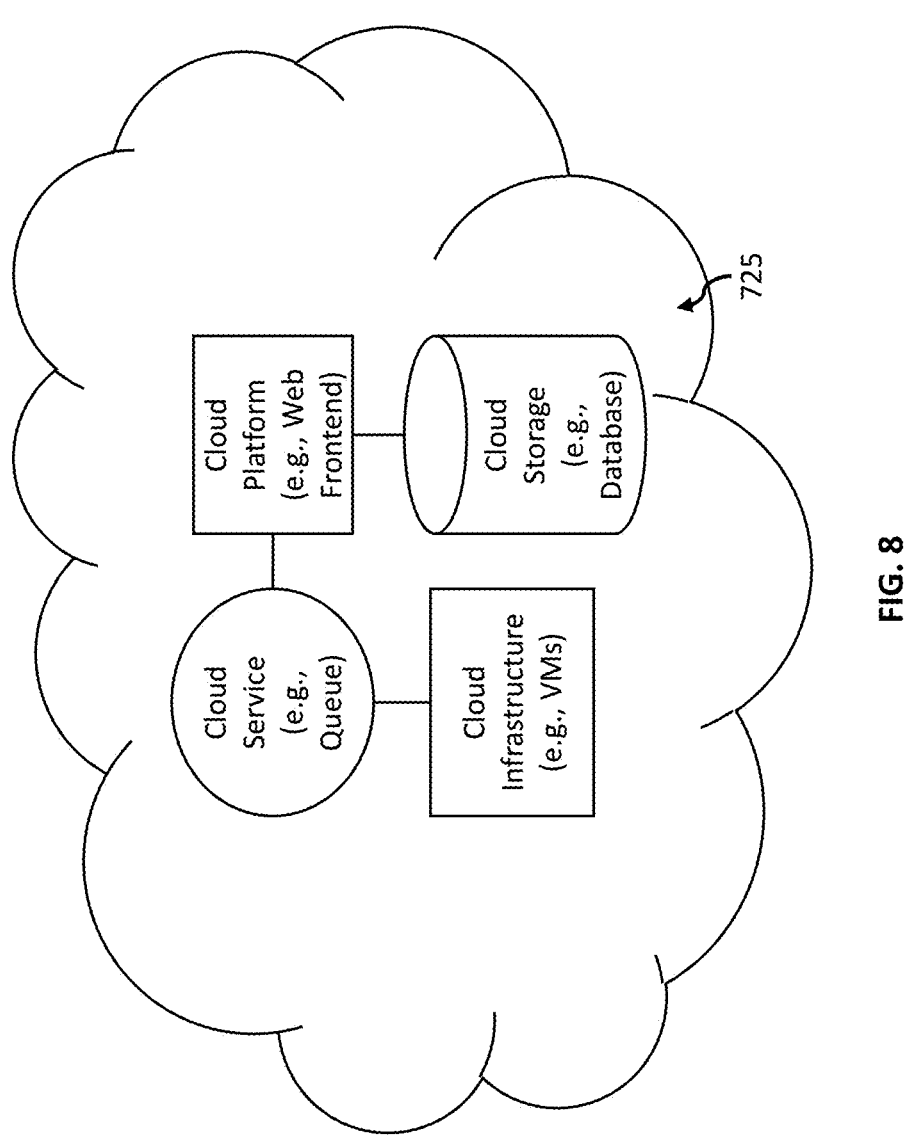
FIG. 8 depicts illustrative schematics of an exemplary implementation of the cloud computing/architecture(s) in which embodiments of a system for disease classification recommendation system may be specifically configured to operate in accordance with some embodiments of the present disclosure.
Figure 9:
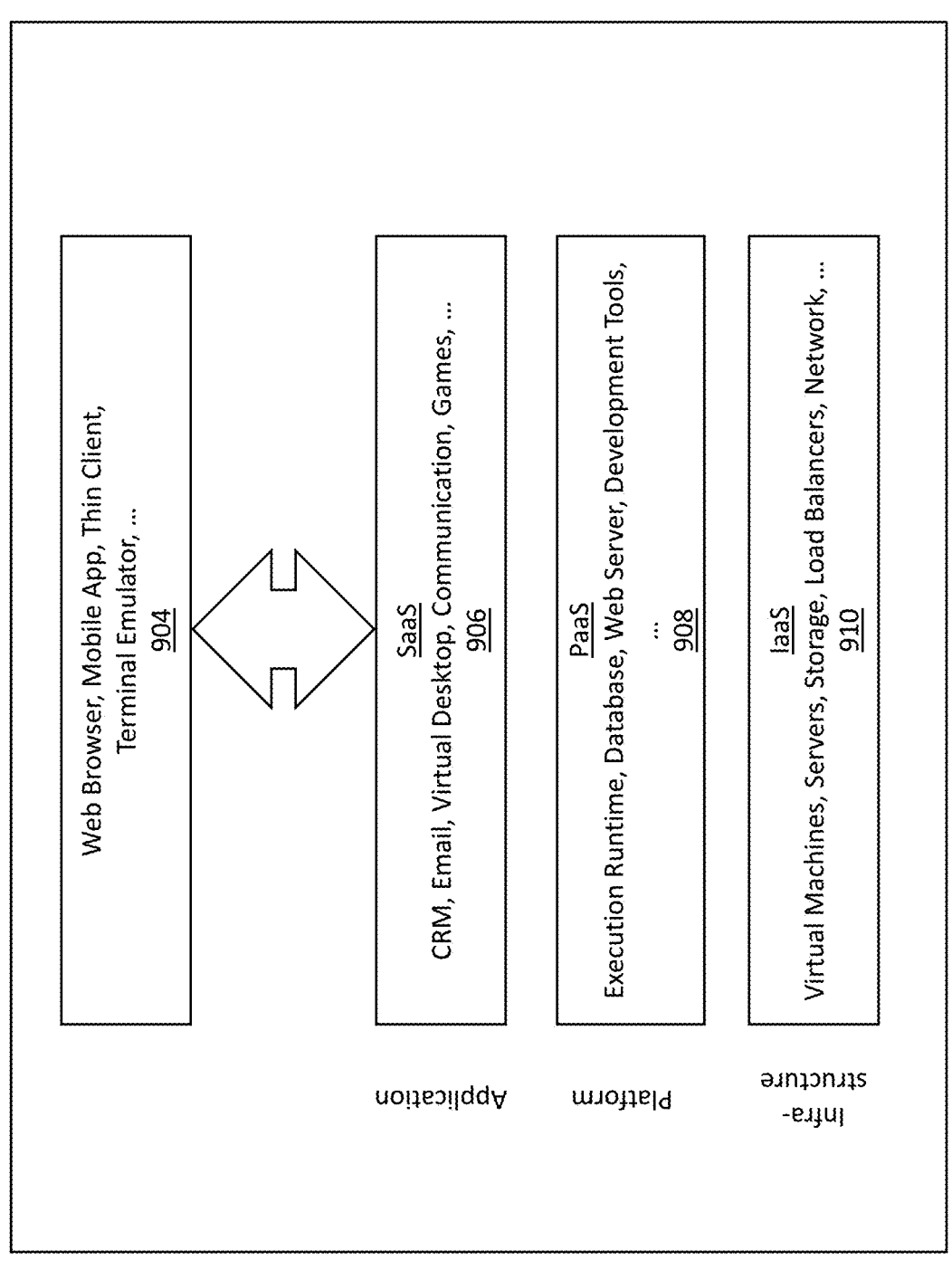
FIG. 9 depicts illustrative schematics of another exemplary implementation of the cloud computing/architecture(s) in which embodiments of a system for disease classification recommendation system may be specifically configured to operate in accordance with some embodiments of the present disclosure.

In some embodiments, the exemplary inventive computer-based systems/platforms, the exemplary inventive computer-based devices, and/or the exemplary inventive computer-based components of the present disclosure may be specifically configured to operate in a cloud computing/architecture 725 such as, but not limiting to: infrastructure a service (IaaS) 910, platform as a service (PaaS) 908, and/or software as a service (Saas) 906 using a web browser, mobile app, thin client, terminal emulator or other endpoint 904. FIGS. 8 and 9 illustrate schematics of exemplary implementations of the cloud computing/architecture(s) in which the exemplary inventive computer-based systems/platforms, the exemplary inventive computer-based devices, the exemplary inventive computer-based devices, and/or the exemplary inventive computer-based components of the present disclosure may be specifically configured to operate.

Figure 10:
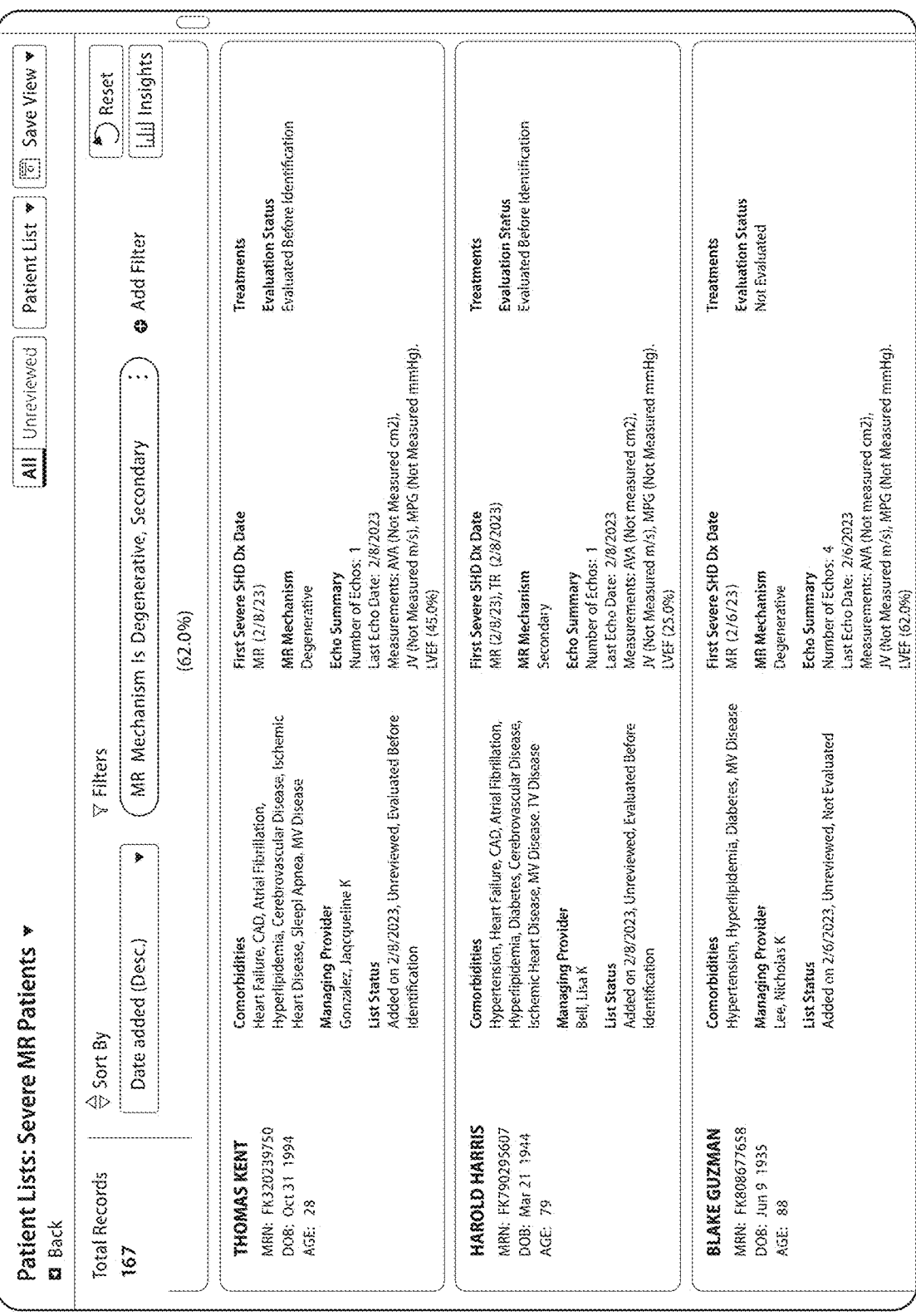
FIG. 10 depicts an illustrative patient information dashboard of a graphical user interface that leverages the patient classification regarding one or more diagnoses in medical reports from one or more embodiments of the disease classification recommendation system in accordance with one or more embodiments of the present disclosure.

Referring now to FIG. 10, an illustrative patient information dashboard of a graphical user interface that leverages the patient classification regarding one or more diagnoses in medical reports from one or more embodiments of the disease classification recommendation system is depicted in accordance with one or more embodiments of the present disclosure.

In some embodiments, the patient information dashboard may present a sortable list that is sortable by date, name, date of birth among other characteristics and/or parameters or any combination thereof. In some embodiments, delineation of primary degenerative MR impacts potential candidate lists for intervention to address a patient's disease. In some embodiments, delineation of secondary MR is key to patient identification for TEER.

Thus, in some embodiments, the dashboard may also include filters for filtering patient records according MR mechanism or other classification of a disease/condition. As detailed above, the classification may be automatically applied to patient records based on processing each patient record with the NLP model(s) 110. Accordingly, filters within patient lists (e.g. Severe MR) allow users to identify cohorts of patients with either primary (degenerative) or secondary MR. such a dashboard may therefore provide the scientific community with deeper insight on diagnosis, treatment and outcome trends for patients with primary (degenerative) vs. secondary MR.

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

In some embodiments, exemplary inventive, specially programmed computing systems and platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes.

In some embodiments, the NFC can represent a short-range wireless communications technology in which NFC-enabled devices are "swiped," "bumped," "tap" or otherwise moved in close proximity to communicate. In some embodiments, the NFC could include a set of short-range wireless technologies, typically requiring a distance of 10 cm or less. In some embodiments, the NFC may operate at 13.56 MHz on ISO/IEC 18000-3 air interface and at rates ranging from 106 kbit/s to 424 kbit/s. In some embodiments, the NFC can involve an initiator and a target; the initiator actively generates an RF field that can power a passive target. In some embodiment, this can enable NFC targets to take very simple form factors such as tags, stickers, key fobs, or cards that do not require batteries. In some embodiments, the NFC's peer-to-peer communication can be conducted when a plurality of NFC-enable devices (e.g., smartphones) within close proximity of each other.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, programs, applications, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores," may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of illustrative computer-based systems or platforms of the present disclosure may include or be incorporated, partially or entirely into at least one personal computer (PC), laptop computer, ultra-laptop computer, tablet, touch pad, portable computer, hand-held computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

In some embodiments, as detailed herein, one or more of the computer-based systems of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a message, a map, an entire application (e.g., a calculator), data points, and other suitable data. In some embodiments, as detailed herein, one or more of the computer-based systems of the present disclosure may be implemented across one or more of various computer platforms such as, but not limited to: (1) FreeBSD, NetBSD, OpenBSD; (2) Linux; (3) Microsoft Windows™; (4) Open VMS™; (5) OS X (MacOS™); (6) UNIX™; (7) Android; (8) iOS™; (9) Embedded Linux; (10) Tizen™; (11) WebOS™; (12) Adobe AIR™; (13) Binary Runtime Environment for Wireless (BREW™); (14) Cocoa™ (API); (15) Cocoa™ Touch; (16) Java™ Platforms; (17) JavaFX™; (18) QNX™; (19) Mono; (20) Google Blink; (21) Apple WebKit; (22) Mozilla Gecko™; (23) Mozilla XUL; (24) .NET Framework; (25) Silverlight™; (26) Open Web Platform; (27) Oracle Database; (28) Qt™; (29) SAP NetWeaver™; (30) Smartface™; (31) Vexi™; (32) Kubernetes™ and (33) Windows Runtime (WinRT™) or other suitable computer platforms or any combination thereof. In some embodiments, illustrative computer-based systems or platforms of the present disclosure may be configured to utilize hard-wired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, illustrative computer-based systems or platforms of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments, illustrative computer-based systems or platforms of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, or objects. For example, such projections may be a visual overlay for a mobile augmented reality (MAR) application.

In some embodiments, illustrative computer-based systems or platforms of the present disclosure may be configured to be utilized in various applications which may include, but not limited to, gaming, mobile-device games, video chats, video conferences, live video streaming, video streaming and/or augmented reality applications, mobile-device messenger applications, and others similarly suitable computer-device applications.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, terms "proximity detection," "locating," "location data," "location information," and "location tracking" refer to any form of location tracking technology or locating method that can be used to provide a location of, for example, a particular computing device, system or platform of the present disclosure and any associated computing devices, based at least in part on one or more of the following techniques and devices, without limitation: accelerometer(s), gyroscope(s), Global Positioning Systems (GPS); GPS accessed using Bluetooth™; GPS accessed using any reasonable form of wireless and non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, Cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed; this is in no way meant to be a limitation.

As used herein, terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

In some embodiments, the illustrative computer-based systems or platforms of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTR0, SHA-1, SHA-2, Tiger (TTH), WHIRLPOOL, RNGs).

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

The aforementioned examples are, of course, illustrative and not restrictive.

At least some aspects of the present disclosure will now be described with reference to the following numbered clauses.

Clause 1. A method, including: receiving, by at least one processor, patient data including at least one written report associated with at least one patient; accessing, by the at least one processor, a dictionary of terminology associated with at least one disease; where the terminology includes a plurality of descriptors; where each descriptor is indicative of at least one category of a plurality of categories associated with the at least one disease; where each descriptor is associated with at least one descriptor-specific score representative of a relevance to the at least one category; inputting, by the at least one processor, the at least one written report into a tokenization function to output a set of tokens, where the tokenization function is configured to: parse at least one word pattern in the at least one written report, and generate the set of tokens from the at least one word pattern; determining, by the at least one processor, a presence in the at least one written report of each descriptor of the plurality of descriptors based at least in part on the set of tokens associated with the at least one written report; determining, by the at least one processor, a category-specific score of a plurality of category-specific scores associated with each category of the plurality of categories based at least in part on: the presence of each descriptor of the plurality of descriptors and the at least one descriptor-specific score of each descriptor; determining, by the at least one processor, at least one category recommendation score indicative of at least one particular category based at least in part on the category-specific score associated with each category; generating, by the at least one processor, at least one category recommendation representing the at least one particular category for the at least one patient based at least in part on the at least one category recommendation score; and rendering, by the at least one processor, an output to a display associated with the at least one patient to present to a user at least one category recommendation associated with the at least one category recommendation score so as to provide clinical decision support.

Clause 2. A system including: at least one processor in communication with at least one non-transitory computer readable medium having software instructions stored thereon, where, upon execution of the software instructions, the at least one processor is configured to: receiving, by at least one processor, patient data including at least one written report associated with at least one patient; access a dictionary of terminology associated with at least one disease; where the terminology includes a plurality of descriptors; where each descriptor is indicative of at least one category of a plurality of categories associated with the at least one disease; where each descriptor is associated with at least one descriptor-specific score representative of a relevance to the at least one category; input the at least one written report into a tokenization function to output a set of tokens, where the tokenization function is configured to: parse at least one word pattern in the at least one written report, and generate the set of tokens from the at least one word pattern; determine a presence in the at least one written report of each descriptor of the plurality of descriptors based at least in part on the set of tokens associated with the at least one written report; determine a category-specific score of a plurality of category-specific scores associated with each category of the plurality of categories based at least in part on: the presence of each descriptor of the plurality of descriptors and the at least one descriptor-specific score of each descriptor; determine at least one category recommendation score indicative of at least one particular category based at least in part on the category-specific score associated with each category; generate at least one category recommendation representing the at least one particular category for the at least one patient based at least in part on the at least one category recommendation score; and render an output to a display associated with the at least one patient to present to a user at least one category recommendation associated with the at least one category recommendation score so as to provide clinical decision support.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added and/or any desired steps may be eliminated).

What is claimed is:

1. A method, comprising:

receiving, by at least one processor associated with at least one electronic health record (EHR) system, patient data comprising at least one written report associated with at least one patient;

accessing, by the at least one processor, a dictionary of terminology associated with mitral regurgitation (MR);

wherein the terminology includes a plurality of descriptors;

wherein each descriptor is indicative of at least one category of a plurality of categories associated with the MR;

parsing, by the at least one processor, at least one word pattern in the at least one written report to produce a set of tokens from the at least one word pattern;

inputting, by the at least one processor, each token in the set of tokens of the plurality of descriptors into a plurality of natural language processing pipelines, each respective natural language processing pipeline being associated with at least one respective detected category of the plurality of categories of the MR and configured to detect, separately and in parallel, at least one respective detected category specific descriptors in the plurality of descriptors, the at least one respective detected category specific descriptors being associated with the at least one respective detected category of the plurality of categories of the MR;

utilizing, by the at least one processor, at least one category-specific rule parameter to determine a category-specific score of a plurality of category-specific scores associated with each category of the plurality of categories;

utilizing, by the at least one processor, at least one recommendation rule parameter to determine at least one recommended category score indicative of at least one particular category of the MR based at least in part on the category-specific score associated with each category;

generating, by the at least one processor, at least one category recommendation representing a particular category of the MR for the at least one patient based at least in part on the at least one recommended category score;

causing to produce, by the at least one processor, graphical user interface (GUI) associated with the EHR, the GUI displaying EHR data for the at least one patient augmented with the at least one recommended category score to present to a user the at least one category recommendation so as to provide clinical decision support for administration of transcatheter edge-to-edge repair (TEER) to effect repair of a mitral valve of the patient in response to the at least one category recommendation for a particular category of the MR of the patient; and administering the TEER to the at least one patient based at least in part on the at least one category recommendation to repair the mitral valve.

2. The method of claim 1, further comprising:

inputting, by the at least one processor, each descriptor of the plurality of descriptors into a tokenization function to output a set of descriptor tokens; and searching, by the at least one processor, the set of tokens with the set of descriptor tokens to identify occurrences of each descriptor based at least in part on a match of at least one descriptor token of each descriptor to at least one token of the written report.

3. The method of claim 1, wherein the plurality of descriptors comprises a plurality of combinations of a plurality of descriptor tokens, wherein each combination of the plurality of combinations represents a particular descriptor of the plurality of descriptors.

4. The method of claim 3, wherein the plurality of combinations and the plurality of descriptor tokens are hand-crafted.

5. The method of claim 1, wherein the plurality of categories associated with mitral regurgitation comprises:

a primary degenerative mitral regurgitation category indicative of primary degenerative mitral regurgitation, and a secondary mitral regurgitation category indicative of secondary mitral regurgitation.

6. The method of claim 5, further comprising:

determining the at least one category recommendation as mixed mitral regurgitation indicative of a combination of the primary degenerative mitral regurgitation and the secondary mitral regurgitation based at least in part on the at least one set of rules indicating a presence of primary degenerative mitral regurgitation and a presence of secondary mitral regurgitation.

7. The method of claim 5, further comprising:

determining the at least one category recommendation as unknown mitral regurgitation based at least in part on the at least one set of rules not indicating a presence of primary degenerative mitral regurgitation and not indicating a presence of secondary mitral regurgitation.

8. The method of claim 1, further comprising:

determining, by the at least one processor, the at least one category recommendation indicative of the at least one particular category based at least in part on:

a category-specific score associated with each category, and at least one medical test result.

9. The method of claim 1, further comprising:

determining, by the at least one processor, the at least one category recommendation indicative of the at least one particular category based at least in part on:

a category-specific score associated with each category, and a set of classification parameters for balancing each category-specific score so as to select a particular category of the plurality of categories.

10. A system comprising:

at least one processor associated with at least one electronic health record (EHR) system and in communication with at least one non-transitory computer readable medium having software instructions stored thereon, wherein, upon execution of the software instructions, the at least one processor is configured to:

receiving, by the at least one processor, patient data comprising at least one written report associated with at least one patient;

accessing, by the at least one processor, a dictionary of terminology associated with mitral regurgitation (MR);

wherein the terminology includes a plurality of descriptors;

wherein each descriptor is indicative of at least one category of a plurality of categories associated with the MR;

parsing, by the at least one processor, at least one word pattern in the at least one written report to produce a set of tokens from the at least one word pattern;

inputting, by the at least one processor, each token in the set of tokens of the plurality of descriptors into a plurality of natural language processing pipelines, each respective natural language processing pipeline being associated with at least one respective detected category of the plurality of categories of the MR and configured to detect, separately and in parallel, at least one respective detected category specific descriptors in the plurality of descriptors, the at least one respective detected category specific descriptors being associated with the at least one respective detected category of the plurality of categories of the MR;

utilizing, by the at least one processor, at least one category-specific rule parameter to determine a category-specific score of a plurality of category-specific scores associated with each category of the plurality of categories;

utilizing, by the at least one processor, at least one recommendation rule parameter to determine at least one recommended category score indicative of at least one particular category of the MR based at least in part on the category-specific score associated with each category;

generating, by the at least one processor, at least one category recommendation representing a particular category of the MR for the at least one patient based at least in part on the at least one recommended category score; and causing to produce, by the at least one processor, graphical user interface (GUI) associated with the EHR, the GUI displaying EHR data for the at least one patient augmented with the at least one recommended category score to present to a user the at least one category recommendation so as to provide clinical decision support for administration of transcatheter edge-to-edge repair (TEER) to effect repair of a mitral valve of the patient in response to the at least one category recommendation for a particular category of the MR of the patient; and administering the TEER to the at least one patient based at least in part on the at least one category recommendation to repair the mitral valve.

11. The system of claim 10, wherein, upon execution of the software instructions, the at least one processor is further configured to:

input each descriptor of the plurality of descriptors into a tokenization function to output a set of descriptor tokens; and search the set of tokens with the set of descriptor tokens to identify occurrences of each descriptor based at least in part on a match of at least one descriptor token of each descriptor to at least one token of the written report.

12. The system of claim 10, wherein the plurality of descriptors comprises a plurality of combinations of a plurality of descriptor tokens, wherein each combination of the plurality of combinations represents a particular descriptor of the plurality of descriptors.

13. The system of claim 12, wherein the plurality of combinations and the plurality of descriptor tokens are hand-crafted.

14. The system of claim 10, wherein the plurality of categories associated with mitral regurgitation comprises:

a primary degenerative mitral regurgitation category indicative of primary degenerative mitral regurgitation, and a secondary mitral regurgitation category indicative of secondary mitral regurgitation.

15. The system of claim 14, wherein, upon execution of the software instructions, the at least one processor is further configured to:

determine the at least one category recommendation as mixed mitral regurgitation indicative of a combination of the primary degenerative mitral regurgitation and the secondary mitral regurgitation based at least in part on at least one set of rules indicating a presence of primary degenerative mitral regurgitation and a presence of secondary mitral regurgitation.

16. The system of claim 14, wherein, upon execution of the software instructions, the at least one processor is further configured to:

determine the at least one category recommendation as unknown mitral regurgitation based at least in part on the at least one set of rules not indicating a presence of primary degenerative mitral regurgitation and not indicating a presence of secondary mitral regurgitation.

17. The system of claim 10, wherein, upon execution of the software instructions, the at least one processor is further configured to:

determine at least one category recommendation indicative of the at least one particular category based at least in part on:

a category-specific score associated with each category, and at least one medical test result.

18. The system of claim 10, wherein, upon execution of the software instructions, the at least one processor is further configured to:

determine at least one category recommendation score indicative of the at least one particular category based at least in part on:

a category-specific score associated with each category, and a set of classification parameters for balancing each category-specific score so as to select a particular category of the plurality of categories.

\* \* \* \* \*